(12) United States Patent
Watanabe et al.

(10) Patent No.: US 9,795,769 B2
(45) Date of Patent: Oct. 24, 2017

(54) BALLOON CATHETER, BALLOON CATHETER MANUFACTURING DEVICE, BALLOON CATHETER MANUFACTURING METHOD, CATHETER CONNECTION DEVICE, CATHETER CONNECTION METHOD, AND CONNECTED CATHETER

(75) Inventors: Kimihiko Watanabe, Tokyo (JP); Hirotoshi Fuse, Tokyo (JP); Takakazu Tomizawa, Tokyo (JP); Yoshiyuki Sugawara, Tokyo (JP); Yoshio Fukamatsu, Tokyo (JP); Eiji Kaneko, Tokyo (JP)

(73) Assignee: SEIDENSHA ELECTRONICS CO., LTD. (JP)

( * ) Notice: Subject to any disclaimer, the term of this patent is extended or adjusted under 35 U.S.C. 154(b) by 268 days.

(21) Appl. No.: 13/508,310

(22) PCT Filed: Dec. 24, 2010

(86) PCT No.: PCT/JP2010/073334
§ 371 (c)(1),
(2), (4) Date: May 4, 2012

(87) PCT Pub. No.: WO2011/125263
PCT Pub. Date: Oct. 13, 2011

(65) Prior Publication Data
US 2012/0226229 A1    Sep. 6, 2012

(30) Foreign Application Priority Data

Apr. 1, 2010 (JP) ................................. 2010-085345

(51) Int. Cl.
*A61M 25/10*    (2013.01)
*B29C 65/16*    (2006.01)
(Continued)

(52) U.S. Cl.
CPC .... *A61M 25/1034* (2013.01); *A61M 25/1036* (2013.01); *B29C 65/1635* (2013.01);
(Continued)

(58) Field of Classification Search
CPC .. A61M 25/10; A61M 25/16; A61M 25/1034; B29C 65/16
(Continued)

(56) References Cited

U.S. PATENT DOCUMENTS 5,501,759 A * 3/1996 Forman ....................... 156/272.8
7,678,223 B2 * 3/2010 Strong .............. A61M 25/0009
156/158
(Continued)

FOREIGN PATENT DOCUMENTS

JP    08-038610    2/1996
JP    09-182796    7/1997
(Continued)

OTHER PUBLICATIONS

JP 2004349123A English machine translation, Dec. 2004.*
Written Opinion (Form PCT/ISA/237) for corresponding International Application PCT/JP2010/073334.

*Primary Examiner* — Michael N Orlando
*Assistant Examiner* — Elizabeth Bradford
(74) *Attorney, Agent, or Firm* — Merchant & Gould P.C.

(57) ABSTRACT

To provide a balloon catheter and an apparatus and method for manufacturing the balloon catheter, whereby the degree of welding can be appropriately adjusted and the balloon catheter can be formed so as to have a desired surface profile suitable for various uses including medical use.
With a shaft 14 inserted through a catheter tube 30a inserted into an end portion 28b of a balloon and also with a pressure tube 32a fitted around a welding section where the end portion 28b of the balloon 28 is lapped over the catheter tube
(Continued)

30a, the shaft 14 is heated by emitting laser light from a laser radiation unit 8 to the welding section while the shaft 14 is rotated by a chuck, to weld the welding section.

8 Claims, 34 Drawing Sheets

(51) Int. Cl.
  *B29C 65/00* (2006.01)
  *B29C 65/18* (2006.01)
  *B29C 65/24* (2006.01)
  *B29L 31/00* (2006.01)

(52) U.S. Cl.
  CPC ...... *B29C 65/1654* (2013.01); *B29C 65/1658* (2013.01); *B29C 65/18* (2013.01); *B29C 65/245* (2013.01); *B29C 66/116* (2013.01); *B29C 66/1122* (2013.01); *B29C 66/1142* (2013.01); *B29C 66/1162* (2013.01); *B29C 66/131* (2013.01); *B29C 66/3472* (2013.01); *B29C 66/5221* (2013.01); *B29C 66/534* (2013.01); *B29C 66/63* (2013.01); *B29C 66/65* (2013.01); *B29C 66/73521* (2013.01); *B29C 66/81267* (2013.01); *B29C 66/81419* (2013.01); *B29C 66/81457* (2013.01); *B29C 66/836* (2013.01); *B29C 66/9161* (2013.01); *B29C 66/9192* (2013.01); *B29C 66/93431* (2013.01); *B29C 66/93451* (2013.01); *B29C 66/71* (2013.01); *B29C 66/73921* (2013.01); *B29C 66/9672* (2013.01); *B29C 66/9674* (2013.01); *B29K 2995/0027* (2013.01); *B29L 2031/7543* (2013.01)

(58) Field of Classification Search
  USPC ........................ 156/272.2, 379.6, 379.8, 391
  See application file for complete search history.

(56) References Cited

U.S. PATENT DOCUMENTS

| | | | |
|---|---|---|---|
| 7,820,936 B2 * | 10/2010 | Weber et al. | 219/121.64 |
| 2003/0032920 A1 * | 2/2003 | Wantink | A61M 25/001 |
| | | | 604/103 |
| 2004/0215141 A1 * | 10/2004 | Clarke | A61M 25/1034 |
| | | | 604/103 |
| 2006/0071371 A1 * | 4/2006 | Quint | B29C 65/18 |
| | | | 264/512 |
| 2007/0060910 A1 * | 3/2007 | Grandt | A61M 25/0009 |
| | | | 604/524 |
| 2008/0135170 A1 * | 6/2008 | He et al. | 156/272.8 |
| 2009/0227962 A1 * | 9/2009 | Eversull | A61L 29/085 |
| | | | 604/265 |

FOREIGN PATENT DOCUMENTS

| | | | | |
|---|---|---|---|---|
| JP | 11-085210 | 3/1999 | | |
| JP | 11-254167 | 9/1999 | | |
| JP | 2001-191412 | 7/2001 | | |
| JP | 2002-301160 | 10/2002 | | |
| JP | 2004-050513 | 2/2004 | | |
| JP | 2004349123 A | * 12/2004 | | ............... F21S 8/10 |
| JP | 2005-334542 | 12/2005 | | |
| JP | 2008-073730 | 4/2008 | | |
| JP | 2008-237844 | 10/2008 | | |
| WO | WO 2005097471 | * 10/2005 | | ............ B29C 65/16 |

* cited by examiner

FIG. 10

| | | No.1 | No.2 | No.3 | No.4 | No.5 | No.6 | No.7 | No.8 | No.9 |
|---|---|---|---|---|---|---|---|---|---|---|
| | Welding Condition | Z0 | Z1 | Z2 | Z0 | Z1 | Z2 | Z0 | Z1 | Z2 |
| Welding Parameters | Laser Spot Diameter (Z) | N1 | N2 | N3 | N1 | N2 | N3 | N1 | N2 | N3 |
| | Heating Shaft Rotating Speed (N) | M | M | M | M | M | M | F | F | F |
| | Laser Radiation Unit: Fixed (F)/Moved (M) | X1 | X1 | X1 | X1 | X1 | X1 | X1 | X1 | X1 |
| | Laser Light Radiation Start Position (X1) | X2 | X2 | X2 | X2 | X2 | X2 | X2 | X2 | X2 |
| | Laser Light Radiation End Position (X2) | V1 | V1 | V1 | V1 | V2 | V2 | V2 | V3 | V4 |
| | Moving Speed (V) | 1 | 1 | 2 | 1 | 1 | 2 | 1 | 1 | 2 |
| | One side (1)/Both Sides (2) | 0 | 0 | L1 | 0 | 0 | L1 | 0 | 0 | L1 |
| | Distance (L) of Movement | PP | PP | PP | PP | PP | PP | PP | PP | PP |
| Material | Substance | T1 | T2 | T3 | T1 | T2 | T3 | T1 | T2 | T3 |
| | Thickness (T) | 95 | 92 | 88 | 84 | 82 | 60 | 55 | 53 | 48 |
| | Evaluation Score | | | | | | | | | |

(EXAMPLE)
DIVIDED INTO 5 INTERVALS

BALLOON CATHETER, BALLOON CATHETER MANUFACTURING DEVICE, BALLOON CATHETER MANUFACTURING METHOD, CATHETER CONNECTION DEVICE, CATHETER CONNECTION METHOD, AND CONNECTED CATHETER

This application is a National Stage Application of PCT/JP2010/073334, filed 24 Dec. 2010, which claims benefit of Serial No. 2010-085345, filed 1 Apr. 2010 in Japan and which applications are incorporated herein by reference. To the extent appropriate, a claim of priority is made to each of the above disclosed applications.

TECHNICAL FIELD

The present invention relates to a balloon catheter used mainly for medical purposes and a manufacturing apparatus and method for manufacturing the balloon catheter.

BACKGROUND ART

A balloon catheter is constituted by a hollow soft tube (hereinafter referred to merely as tube) and an inflatable balloon (hereinafter referred to merely as balloon) attached to a distal end of the tube.

Such a balloon catheter is used mainly for medical purposes. Medical treatment using the balloon catheter includes, for example, PTCA (percutaneous transluminal coronary angioplasty). In PTCA, a thin wire called guide wire is inserted through to a narrowed affected area of the body, and a balloon is guided along the guide wire up the affected area, where the balloon is inflated to enlarge the affected area.

In this manner, the balloon catheter is inserted into the body of a human or animal through a blood vessel or the like, and thus need to have a smooth profile so as not to damage tissue in the body.

Generally, the balloon catheter is produced in the following manner: A cylindrical balloon is prepared which has a large-diameter body at its central portion and small-diameter portions at opposite ends of the body, and a catheter tube is inserted into each of the opposite end portions of the balloon and is welded to the end portion by applying heat, or bonded to the end portion by an adhesive.

For example, a balloon catheter manufacturing method has been known in which laser light is radiated onto the end portions of the balloon for fusion bonding (see Patent Document 1 identified below). In Patent Document 1, laser light of the far-infrared region is converged using a lens so as to impinge upon and weld the boundary between the catheter tube (tubular catheter) and the tip of the end portion of the balloon (inflatable balloon).

PRIOR ART LITERATURE

Patent Document

Patent Document 1: Published Japanese Patent Application No. 09-182796

SUMMARY OF THE INVENTION

Problems to be Solved by the Invention

According to the technique disclosed in Patent Document 1, the laser light is focused on the boundary between the catheter tube and the balloon to heat the two at the same time. Generally, however, the balloon has a smaller thickness than the catheter tube, and as the boundary is heated, the balloon is melted and broken earlier than the catheter tube. Also, a laser configured to emit laser light of the far-infrared region has high output, and it is difficult to adjust the laser output. In Patent Document 1, therefore, the speed of rotating the balloon catheter is increased during the welding, but a problem still arises in that it is difficult to minutely adjust the degree of welding.

Also, in Patent Document 1, a heat-shrinkable tube (thermally shrinkable tube) is used to apply pressure to the balloon and the catheter tube. Generally, however, the heat-shrinkable tube is readily affected by temperature in the environment of usage and thus is difficult to handle. Further, since the heat-shrinkable tube is deformed as it shrinks, the pressure application position is displaced or the shrinkage takes place in a nonuniform manner, possibly creating unevenness or a level difference on the fusion bonded surface. Moreover, a problem also arises in that it is difficult to remove the heat-shrunk tube after the welding.

Thus, with the method of converging laser light of the far-infrared region on the boundary between the catheter tube and the balloon and welding the boundary fitted with a heat-shrinkable tube, it is not easy to finish the welding section to a desired shape. If a produced balloon catheter has unevenness on its surface, then it is not suitable for medical use.

The present invention was created to solve the above problems, and an object thereof is to provide a balloon catheter and an apparatus and method of manufacturing the balloon catheter, whereby the degree of welding can be finely and properly adjusted, and the welding can be executed without the need to use a heat-shrinkable tube, which is difficult to handle, to obtain a balloon catheter which has a desired surface profile free from unevenness or a level difference on the fusion bonded surface and thus is suited for use, especially for medical use.

Means for Solving the Problems

To achieve the above object, there is provided a balloon catheter manufacturing apparatus for welding a catheter tube, which is inserted into an end portion of a cylindrical balloon, to the end portion of the balloon. The balloon catheter manufacturing apparatus comprises: a heating shaft inserted through the catheter tube and capable of generating heat when irradiated with laser light; a heating shaft rotation unit configured to rotate the heating shaft while supporting the heating shaft; a laser radiation unit configured to emit the laser light that penetrates through the balloon and the catheter tube and form an irradiation region of a predetermined size on an outer peripheral surface of the heating shaft; an annular pressure member made of an elastic material capable of transmitting the laser light therethrough, the pressure member being fitted around the end portion of the balloon to apply pressure to the end portion of the balloon toward an axis thereof; and a welding controller configured to operate, with the end portion of the balloon lapped over the catheter tube fitted around the heating shaft and with the pressure member fitted around a welding section where the end portion of the balloon is lapped over the catheter tube, to cause the laser radiation unit to emit the laser light so as to form the irradiation region of the predetermined size on the outer peripheral surface of the heating shaft located radially inward of the welding section constituted by the end portion of the balloon and the catheter tube, while causing the heating shaft rotation unit to rotate the heating shaft, to heat the heating shaft and weld the welding section.

The balloon catheter manufacturing apparatus may further comprise a laser supporting unit configured to movably support the laser radiation unit, wherein the laser radiation unit is capable of varying an output of the laser light emitted therefrom, and the welding controller controls the laser supporting unit and the laser radiation unit such that the output of the laser light is high at a tip of the end portion of the balloon and lowers with decreasing distance to a center of the balloon, to weld the welding section.

The balloon catheter manufacturing apparatus may further comprise: a camera configured to acquire an image of the welding section where the catheter tube is inserted into the end portion of the cylindrical balloon; a monitor configured to display the image acquired by the camera; a storage capable of registering predetermined information therein; a registration-readout unit configured to register and read out a laser light radiation start position and a laser light radiation end position in and from the storage; and a laser supporting unit configured to movably support the laser radiation unit, wherein the welding controller registers the laser light radiation start and end positions in the storage by using the registration-readout unit while the image acquired by the camera is displayed on the monitor, and when welding is to be executed, the welding controller reads out the laser light radiation start and end positions from the storage by using the registration-readout unit, and causes the laser light to be radiated on the welding section where the end portion of the balloon is lapped over the catheter tube, from the laser light radiation start position to the laser light radiation end position by using the laser supporting unit, to weld the welding section.

In the balloon catheter manufacturing apparatus, the welding controller may register a predetermined position between the laser light radiation start and end positions and a welding condition applied to the predetermined position in the storage by using the registration-readout unit, and reads out the registered welding condition from the storage to weld the welding section under the welding condition thus read out.

In the balloon catheter manufacturing apparatus, the welding controller may register an evaluation result obtained by actually executing welding under each welding condition registered in the storage, in a manner associated with the corresponding welding condition, and when the welding conditions are read out from the storage, the welding controller causes the monitor to display the welding conditions in descending order of the evaluation results so that a desired one of the welding conditions can be selected.

Also, there is provided a balloon catheter manufacturing method for manufacturing a balloon catheter by welding an end portion of a cylindrical balloon to a catheter tube inserted into the end portion of the balloon, wherein, with a heating shaft, which is capable of generating heat when irradiated with laser light, inserted through the catheter tube inserted into the end portion of the balloon and also with an annular pressure member, which is made of an elastic material capable of transmitting the laser light therethrough, fitted around a welding section where the end portion of the balloon is lapped over the catheter tube, the laser light capable of penetrating through the end portion of the balloon and the catheter tube is emitted from a laser radiation unit such that an irradiation region of a predetermined size is formed on an outer peripheral surface of the heating shaft located radially inward of the welding section constituted by the end portion of the balloon and the catheter tube, while the heating shaft is rotated by a heating shaft rotation unit, to heat the heating shaft and weld the welding section.

Further, there is provided a balloon catheter manufactured by the balloon catheter manufacturing method by inserting a catheter tube into an end portion of a cylindrical balloon and then welding the end portion of the balloon and the catheter tube together, wherein at a welded section where the end portion of the balloon and the catheter tube are welded together, a tip of the end portion of the balloon is fused into and bonded to the catheter tube such that an outer diameter at the tip of the end portion of the balloon is equal to that of the catheter tube.

Furthermore, there is provided a catheter connection apparatus for connecting a pair of catheter tubes end to end. The catheter connection apparatus comprises: a heating shaft inserted through the pair of catheter tubes and capable of generating heat when irradiated with laser light; a heating shaft rotation unit configured to rotate the heating shaft while supporting the heating shaft; a laser radiation unit configured to emit the laser light that penetrates through end portions of the pair of catheter tubes and form an irradiation region of a predetermined size on an outer peripheral surface of the heating shaft; an annular pressure member made of an elastic material capable of transmitting the laser light therethrough, the pressure member being fitted around the end portions of the pair of catheter tubes to apply pressure to the end portions of the pair of catheter tubes toward an axis thereof; and a welding controller configured to operate, with the heating shaft inserted through the pair of catheter tubes and with the pressure member fitted around a welding section where the end portions of the pair of catheter tubes are butted against each other, to cause the laser radiation unit to emit the laser light so as to form the irradiation region of the predetermined size on the outer peripheral surface of the heating shaft located radially inward of the welding section constituted by the pair of catheter tubes, while causing the heating shaft rotation unit to rotate the heating shaft, to heat the heating shaft and weld the welding section.

The catheter connection apparatus may further comprise a laser supporting unit configured to movably support the laser radiation unit, wherein the laser radiation unit is capable of varying an output of the laser light emitted therefrom, and the welding controller controls the laser supporting unit and the laser radiation unit such that the output of the laser light is increased or decreased at a predetermined position of the welding section, to weld the welding section.

The catheter connection apparatus may further comprise: a camera configured to acquire an image of the welding section where the end portions of the pair of catheter tubes are butted against each other; a monitor configured to display the image acquired by the camera; a storage capable of registering predetermined information therein; a registration-readout unit configured to register and read out a laser light radiation start position and a laser light radiation end position in and from the storage; and a laser supporting unit configured to movably support the laser radiation unit, wherein the welding controller registers the laser light radiation start and end positions in the storage by using the registration-readout unit while the image acquired by the camera is displayed on the monitor, and when welding is to be executed, the welding controller reads out the laser light radiation start and end positions from the storage by using the registration-readout unit, and causes the laser light to be radiated on the welding section where the end portions of the pair of catheters are butted against each other, from the laser light radiation start position to the laser light radiation end position by using the laser supporting unit, to weld the welding section.

In the catheter connection apparatus, the welding controller may register a predetermined position between the laser light radiation start and end positions and a welding condition applied to the predetermined position in the storage by using the registration-readout unit, and reads out the registered welding condition from the storage to weld the welding section under the welding condition thus read out.

In the catheter connection apparatus, the welding controller may register an evaluation result obtained by actually executing welding under each welding condition registered in the storage, in a manner associated with the corresponding welding condition, and when the welding conditions are read out from the storage, the welding controller causes the monitor to display the welding conditions in descending order of the evaluation results so that a desired one of the welding conditions can be selected.

Also, there is provided a catheter connection method for connecting a pair of catheter tubes end to end, wherein, with a heating shaft, which is capable of generating heat when irradiated with laser light, inserted through the pair of catheter tubes and also with an annular pressure member, which is made of an elastic material capable of transmitting the laser light therethrough, fitted around a welding section where end portions of the pair of catheter tubes are butted against each other, the laser light capable of penetrating through the welding section constituted by the pair of catheter tubes is emitted from a laser radiation unit such that an irradiation region of a predetermined size is formed on an outer peripheral surface of the heating shaft located radially inward of the welding section constituted by the pair of catheter tubes, while the heating shaft is rotated by a heating shaft rotation unit, to heat the heating shaft and weld the welding section.

Further, there is provided a catheter obtained by the catheter connection method by connecting a pair of catheter tubes end to end by welding, wherein at a welded section where the end portions of the pair of catheter tubes are welded together, the end portions of the pair of catheter tubes are fused and bonded together such that the end portions of the pair of catheter tubes have an identical outer diameter.

Advantageous Effects of the Invention

With the balloon catheter manufacturing apparatus and method, the laser light may penetrate through the balloon and the catheter tube and heat the heating shaft so that the catheter tube may be heated from the radially inward side. It is therefore possible to prevent the balloon from being excessively heated, whereby the welding can be carried out without entailing breakage or the like of the balloon.

Also, while the catheter tube is heated from the radially inward side, the end portion of the balloon and the catheter tube are applied with pressure toward the axis by a pressure tube made of an elastic material and serving as the pressure member, and therefore, the end portion of the balloon is fused into and bonded to the catheter tube. The pressure tube applies pressure by making use of its elastic force, and not thermal shrinkage. Accordingly, the pressure application position is not displaced or an awkward situation where it is difficult to remove the pressure tube after the welding does not occur. The welding section can therefore be applied with pressure uniformly and welded without any unevenness remaining on the welded surface.

Consequently, the joint between the balloon and the catheter tube can be formed into a desired surface profile suited for use, thus making it possible to manufacture balloon catheters which can be satisfactorily used for medical purposes.

With the balloon catheter manufacturing apparatus, the laser radiation unit may be movable, and since the output of the laser light may be variable, the welding can be executed under conditions matching the object to be welded. Where the welding is executed such that the output of the laser light is set high at the tip of the balloon and is lowered with distance toward the center of the balloon, the extent to which the shaft is heated, and thus the extent to which the end portion of the balloon is fused become smaller with distance toward the center of the balloon. It is therefore possible to obtain a balloon catheter having a shape such that the outer diameter at the tip of the end portion of the balloon is equal to that of the catheter tube and smoothly increases toward the center of the balloon.

The balloon catheter manufacturing apparatus may include the storage, the registration-readout unit configured to register and read out the laser light radiation start and end positions in and from the storage, and the laser supporting unit configured to movably support the laser radiation unit. The laser light radiation start and end positions are registered in the storage while the image acquired by the camera is displayed on the monitor, and when the welding is to be executed, the laser light radiation start and end positions are read from the storage, and the laser light is radiated onto the welding section from the laser light radiation start position to the laser light radiation end position by using the laser supporting unit.

In the balloon catheter manufacturing apparatus, a predetermined position between the laser light radiation start and end positions and a welding condition applied to the predetermined position may be registered in the storage. The welding condition can be so set in advance as to change step by step or continuously from the laser light radiation start position to the laser light radiation end position. Thus, with the balloon catheter manufacturing apparatus 4, the welding section of the balloon catheter can be easily formed into a desired surface profile.

With the balloon catheter manufacturing apparatus, welding conditions for welding balloon catheters with various dimensions and shapes can be registered in the storage together with evaluation results obtained by actually executing the welding under the respective welding conditions, and can be read from the storage and displayed on the monitor in descending order of the evaluation results. Since a desired welding condition matching the welding operation to be executed can be selected from among those displayed on the monitor, it is possible to manufacture desired balloon catheters with high quality in a stable manner.

In the balloon catheter, the joint between the end portion of the balloon and the catheter tube may have a smooth profile without any level difference or unevenness. Thus, the balloon catheter can be satisfactorily used for medical purposes and ensure safe medical treatment without damaging tissue in the body when inserted into a blood vessel or the like.

In the catheter connection apparatus and method, with the heating shaft inserted through the pair of catheter tubes and with the pressure member fitted around the welding section where the end portions of the pair of catheter tubes are butted against each other, the laser light is emitted from the laser radiation unit so as to form an irradiation region of the predetermined size on the outer peripheral surface of the heating shaft located radially inward of the welding section constituted by the pair of catheter tubes, while the heating shaft is rotated by the heating shaft rotation unit, to heat the heating shaft and weld the welding section. The welding section can therefore be welded so as to have a surface profile free of unevenness.

With the catheter connection apparatus, the laser radiation unit may be movable and also the output of the laser light is variable. Accordingly, the welding can be executed under a welding condition matching a specified position of the welding section.

In the catheter connection apparatus, the laser light radiation start and end positions can be registered in the storage while the image acquired by the camera is displayed on the monitor, and when the welding is to be executed, the laser light radiation start and end positions can be read from the storage, and the laser light can be radiated onto the welding section from the laser light radiation start position to the laser light radiation end position by using the laser supporting unit.

In the catheter connection apparatus, a predetermined position between the laser light radiation start and end positions and a welding condition applied to the predetermined position can be registered in the storage. The welding condition can therefore be set in advance so as to change step by step or continuously from the laser light radiation start position to the laser light radiation end position.

In the catheter connection apparatus, when the welding conditions are read out from the storage, the read welding conditions may be displayed on the monitor in descending order of the evaluation score so that a desired welding condition can be selected.

Thus, with the catheter connection apparatus, the welding section of the catheters can be easily formed into a desired surface profile.

In the catheter, the end portions of the pair of catheters may be connected to each other so as to have a smooth surface profile without any level difference or unevenness. Thus, the catheter can be satisfactorily used for medical purposes and ensure safe medical treatment without damaging tissue in the body when inserted in a blood vessel or the like.

BRIEF DESCRIPTION OF THE DRAWINGS

FIG. 10 illustrates a data structure of welding conditions for the balloon catheter, stored in a memory 25.

MODE OF CARRYING OUT THE INVENTION

Embodiment 1

Embodiments of the present invention will be described below with reference to the accompanying drawings.

Figure 1:
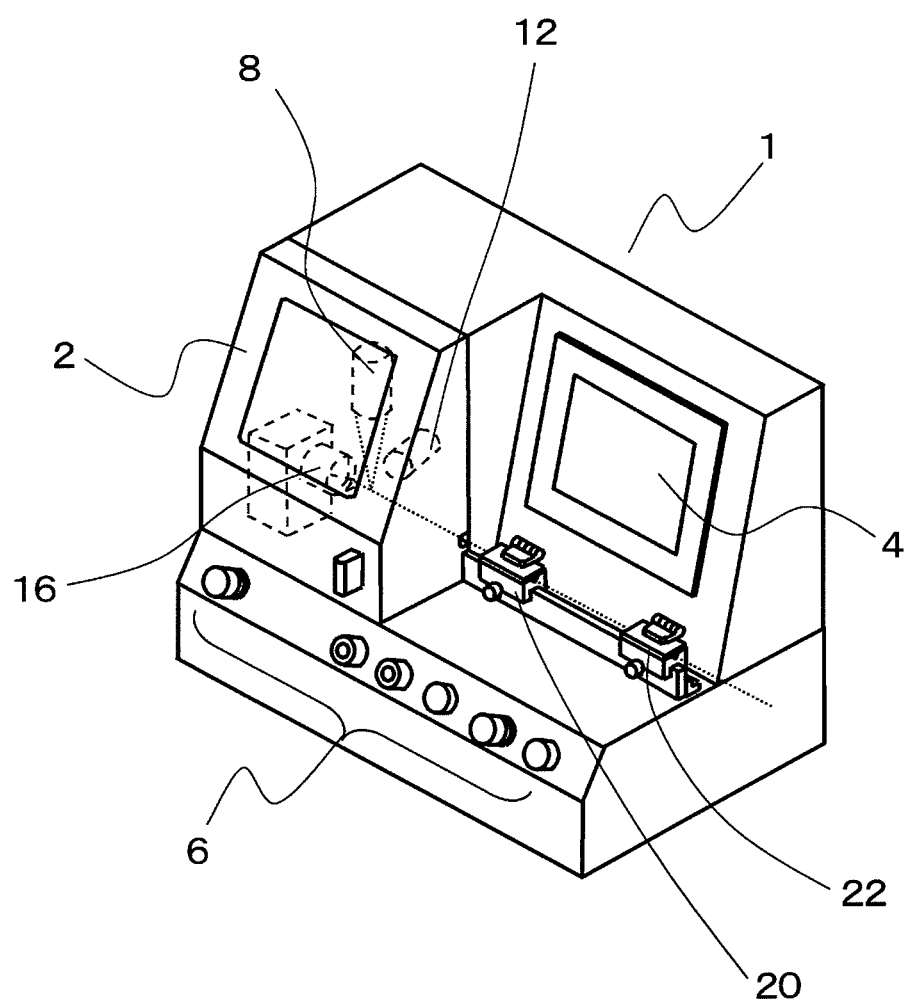
FIG. 1 is a perspective view illustrating an external appearance of a balloon catheter manufacturing apparatus.

FIG. 1 is a perspective view illustrating an external appearance of a balloon catheter manufacturing apparatus according to Embodiment 1 of the present invention.

As illustrated in FIG. 1, the balloon catheter manufacturing apparatus 1 includes, as its external components, a cover 2 for covering a location where a welding operation is performed, a monitor 4 for displaying information about the welding operation, and a welding manipulator 6 used for making various settings related to the welding operation.

Figure 2:
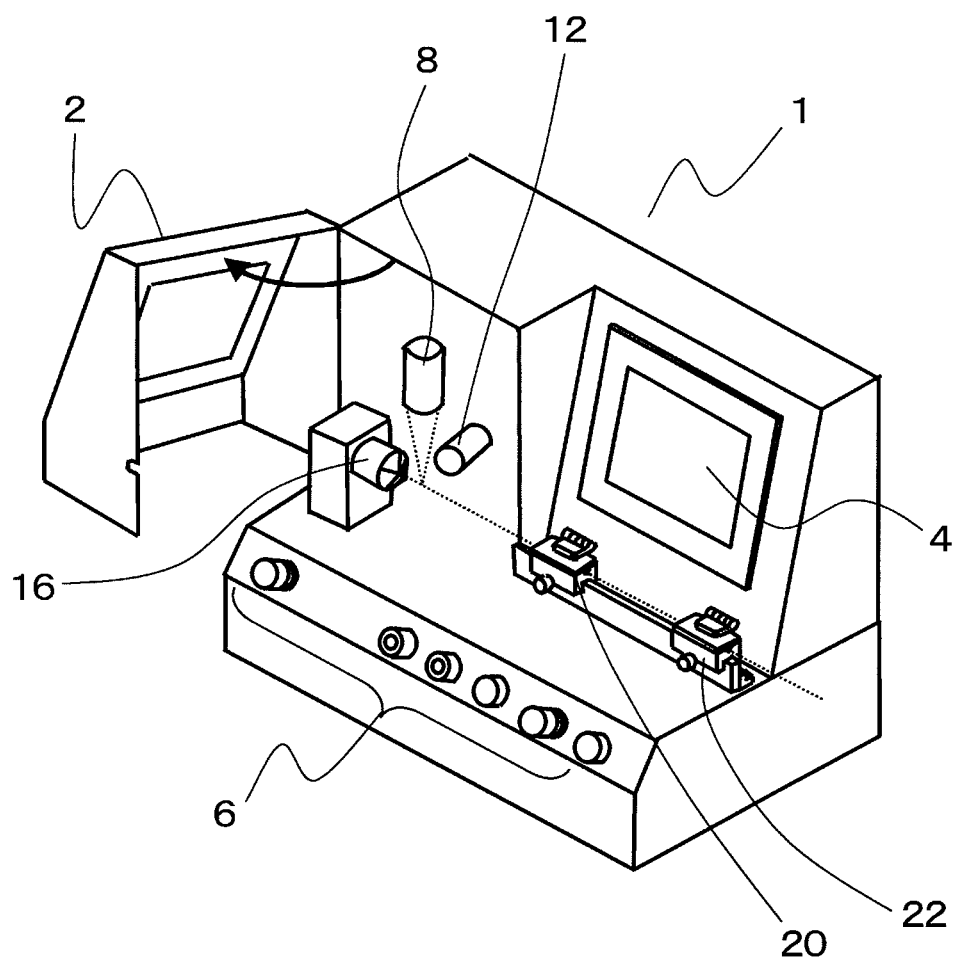
FIG. 2 is a perspective view also illustrating an external appearance of the balloon catheter manufacturing apparatus.

The cover 2 can be opened and closed, and with the cover 2 closed, the welding operation is carried out inside the cover 2. FIG. 2 is a perspective view also illustrating an external appearance of the balloon catheter manufacturing apparatus 1 with the cover 2 opened. In FIG. 2, a chuck 16 (heating shaft rotation unit) for holding and rotating a shaft 14 (heating shaft), not shown, at a predetermined rotational speed, a laser radiation unit 8 and a camera 12 are illustrated only schematically so that their relative positions may be understood. The cover 2 serves to prevent entry of dust or the operator's hand during the welding operation and also to block laser light, thereby ensuring safety of the welding operation.

The monitor 4 is a touch panel and enables various operations in conjunction with information displayed thereon, besides the operations that can be performed by the welding manipulator 6.

The welding manipulator 6 includes a power button for powering on and off the balloon catheter manufacturing apparatus 1, an adjustment-registration button for adjusting and registering a laser light radiation start position (welding start position) or a laser light radiation end position (welding end position), a manual operation button, an emergency stop button, and a welding start button.

An internal arrangement of the balloon catheter manufacturing apparatus 1 will be now described.

Figure 3:
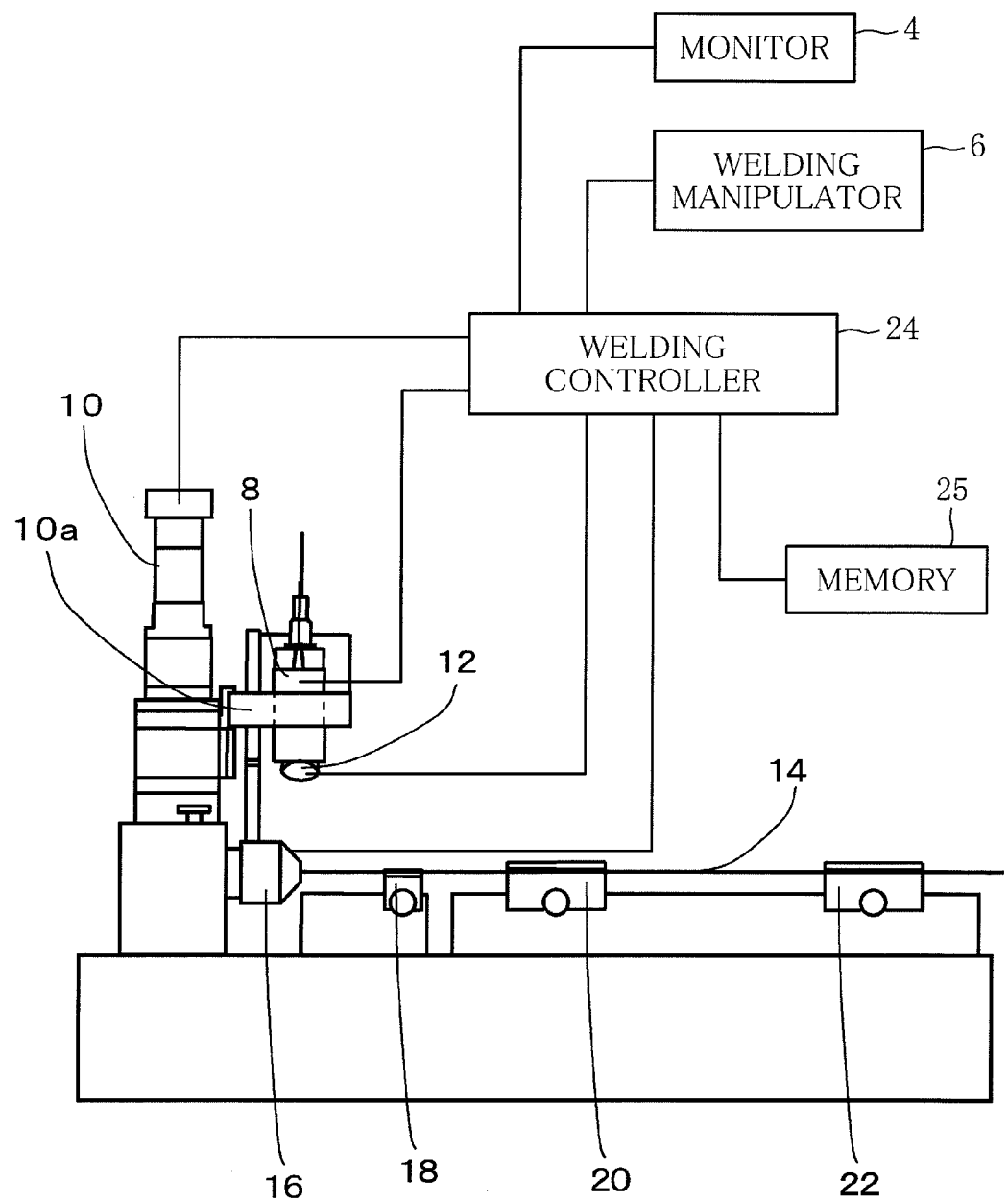
FIG. 3 schematically illustrates an internal arrangement of the balloon catheter manufacturing apparatus.

FIG. 3 schematically illustrates the internal arrangement of the balloon catheter manufacturing apparatus according to the present invention.

As illustrated in FIG. 3, the balloon catheter manufacturing apparatus 1 includes, in its interior, the laser radiation unit 8 for radiating laser light onto an object to be welded, a laser supporting unit 10 for movably supporting the laser radiation unit 8, the camera 12 for acquiring an image of a laser irradiation position, the shaft 14 (heating shaft) extending in one direction, the chuck 16 (heating shaft rotation unit) supporting one end of the shaft 14 and capable of rotating the shaft 14, and three shaft guides 18, 20 and 22 for supporting the shaft 14 at its intermediate and other end portions. The three shaft guides will be hereinafter referred to, in order of the distance from the chuck 16, as front shaft guide 18, center shaft guide 20 and rear shaft guide 22, respectively. The center and rear shaft guides 20 and 22 are located below the monitor 4, as illustrated in FIG. 1. The above elements except the center and rear shaft guides 20 and 22 are arranged inside the cover 2.

Various devices including the monitor 4, the welding manipulator 6, the laser radiation unit 8, the laser supporting unit 10 and the camera 12 are electrically connected to a welding controller 24.

The various devices will be explained in detail. The laser radiation unit 8 is a semiconductor laser, for example, and is directed downward so as to emit laser light to the shaft 14 fixed on the chuck 16. The laser light is emitted from the laser radiation unit 8 so as to converge in conical form and concentrate at a predetermined point near the shaft 14. The laser light has a wavelength ranging from 700 nm to 1200 nm, preferably, from 800 nm to 1000 nm.

The laser supporting unit 10 has an arm 10a coupled to the laser radiation unit 8 and is capable of moving the laser radiation unit 8, together with the arm 10a, in a vertical direction (Z-axis direction) perpendicular to the shaft 14 as well as in a horizontal direction (X-axis direction) identical with the direction in which the shaft 14 extends.

The camera 12 is, for example, a CCD camera and acquires a moving image of the laser irradiation position. The camera 12 is supported so as to be movable while keeping pace with the movement of the laser supporting unit 10 in the X-axis direction. Thus, when the laser radiation unit 8 is moved in the X-axis direction, the camera 12 is able to keep capturing the image of the laser irradiation position.

The shaft 14 generates heat when irradiated with the laser light from the laser radiation unit 8 and is constituted, for example, by a wire of stainless steel.

The chuck 16 supports one end of the shaft 14 such that the shaft 14 extends along the X axis, and also rotates the shaft 14 about its axis.

The front, center and rear shaft guides 18, 20 and 22 rotatably support respective intermediate and other end portions of the shaft 14.

The welding controller 24 is input with information from the various devices electrically connected thereto, and controls the various devices in accordance with the information. For example, the welding controller 24 causes the monitor 4 to display the video image acquired by the camera 12. Also, in accordance with operations performed using the welding manipulator 6 or the monitor 4, the welding controller 24 controls the operation of corresponding devices. Specifically, as control operation with respect to the laser radiation unit 8, the welding controller 24 adjusts the output of the laser light, adjusts the laser irradiation position by moving the laser radiation unit 8 in the X-axis direction relative to the laser supporting unit 10, and adjusts a laser irradiation area by moving the laser radiation unit 8 in the Z-axis direction relative to the laser supporting unit 10. Further, the welding controller 24 adjusts the rotational speed of the chuck 16 to thereby control the time for which the welding object is irradiated with the laser light.

Various parameters related to the output adjustment of the laser light, the movement of the laser radiation unit 8 in the Z- and X-axis directions and the rotational speed of the chuck 16 are set in advance by the operator. The parameters may be set so that the output of the laser light may be variable with progress of the welding, for example.

A balloon catheter, which is an object to be welded, will be now described.

Figure 4:
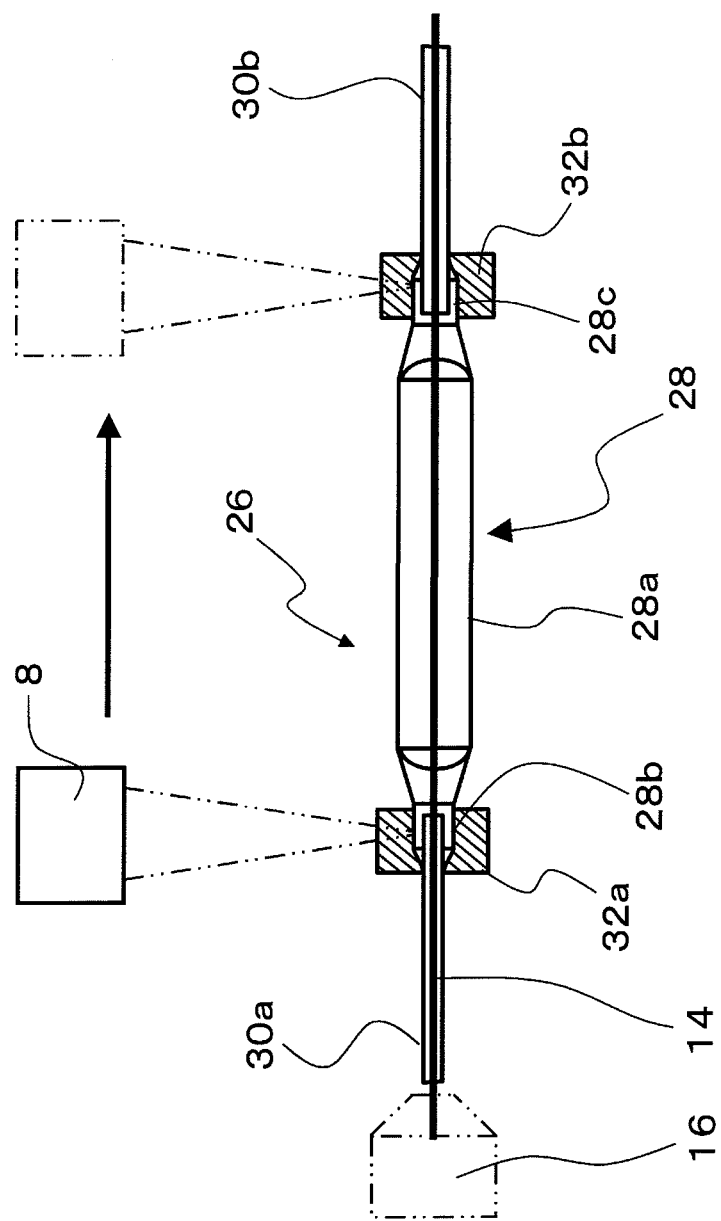
FIG. 4 schematically illustrates a balloon catheter set in the balloon catheter manufacturing apparatus.

FIG. 4 schematically illustrates a balloon catheter set in the balloon catheter manufacturing apparatus.

As illustrated in FIG. 4, the balloon catheter 26 is constituted by a balloon 28 which is inflatable from a deflated or folded state, and catheter tubes 30a and 30b inserted into respective opposite end portions 28b and 28c of the balloon 28.

Specifically, the balloon 28 has a body 28a which is in the form of a cylinder with a large diameter when inflated and which tapers at both ends toward an axis thereof, and the opposite end portions 28b and 28c continuous with the body 28a are each in the form of a cylinder with a small diameter. The balloon 28 is made of a flexible and transparent resin material capable of transmitting the laser light emitted from the laser radiation unit 8 therethrough, such as polyester, polyolefin, polyamide, or thermoplastic polyurethane.

The catheter tubes 30a and 30b are each a tubular member having an outer diameter nearly equal to the inner diameter of the end portions 28b and 28c of the balloon 28 and having an inner diameter nearly equal to the diameter of the aforementioned shaft 14. The catheter tubes 30a and 30b are also made of a flexible and transparent resin material capable of transmitting the laser light therethrough. Further, the catheter tubes 30a and 30b have a thickness larger than that of the balloon 28. The balloon 28 and the catheter tubes 30a and 30b may be made of any desired material insofar as the balloon 28 and the catheter tubes 30a and 30b can transmit the laser light therethrough. For example, the catheter tubes 30a and 30b may be made of a material that generates heat upon absorption of the laser light. Also, the balloon 28 and the catheter tubes 30a and 30b need not be transparent and may be slightly colored. For example, the balloon 28 or the catheter tubes 30a and 30b may be made of a material which is slightly colored in black or the like and thus generates heat to a certain extent when irradiated with the laser light, insofar as the laser light can penetrate through the catheter tubes 30a and 30b.

The catheter tubes 30a and 30b are inserted into the respective end portions 28b and 28c of the balloon 28. Overlaps between the end portions 28b and 28c of the balloon 28 and the respective catheter tubes 30a and 30b are welding sections which are to be welded together.

When the welding sections are welded by the balloon catheter manufacturing apparatus 1, the aforementioned shaft 14 is inserted through the catheter tubes 30a and 30b each forming the inner side of the corresponding welding section, and pressure tubes 32a and 32b are fitted around the respective end portions 28b and 28c of the balloon 28 so as to cover the end portions 28b and 28c each forming the outer side of the corresponding welding section, as well as portions of the respective catheter tubes 30a and 30b.

The pressure tubes 32a and 32b are made of an elastic material capable of transmitting the laser light therethrough, for example, silicone (silicone rubber). Also, the pressure tubes 32a and 32b are each annular in shape and have an inner diameter slightly smaller than the outer diameter of the end portions 28b and 28c of the balloon 28. Thus, when the pressure tubes 32a and 32b are fitted around the end portions 28b and 28c of the balloon 28, the end portions 28b and 28c and the catheter tubes 32a and 32b are applied with pressure radially inward by the elastic force of the pressure tubes 32a and 32b toward the axis, namely, toward the shaft 14. Further, the pressure tubes 32a and 32b are fitted around the end portions 28b and 28c of the balloon 28 and the catheter tubes 30a and 30b so as to cover at least the respective welding sections, and therefore, small empty spaces are created due to the difference in level between the end portions 28b and 28c and the respective catheter tubes 30a and 30b.

With the shaft 14 and the pressure tubes 32a and 32b thus fitted, the balloon catheter 26 is set in the balloon catheter manufacturing apparatus 1. At this time, the balloon 28 is positioned between the chuck 16 and the front shaft guide 18, one end of the shaft 14 is held by the chuck 16, and the remaining portion of the shaft 14 is supported by the shaft guides 18, 20 and 22.

Figure 5:
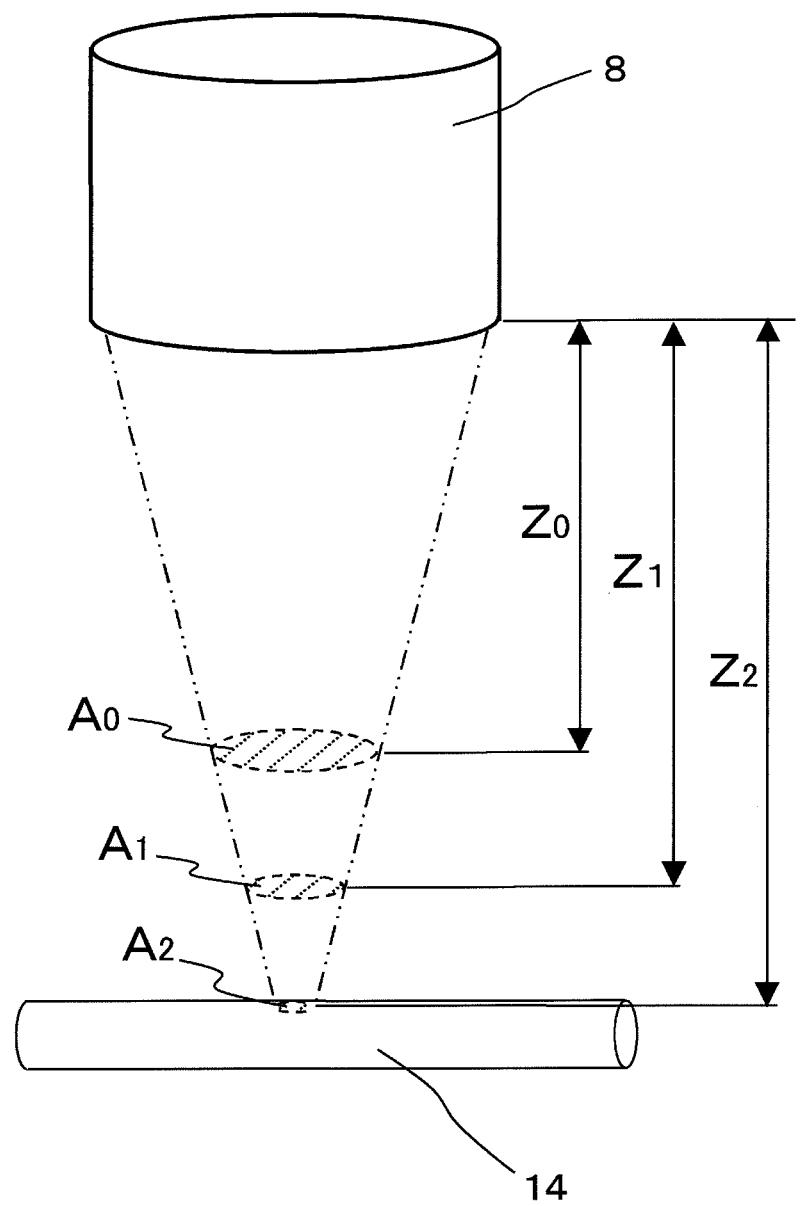
FIG. 5 is a conceptual diagram illustrating the relationship between the distance from a laser light source and the size of a laser irradiation region.

The following describes a welding method by means of the balloon catheter manufacturing apparatus 1 in which is set the balloon catheter 26 not welded yet. FIG. 5 is a conceptual diagram illustrating the relationship between the distance from the laser radiation unit 8 as a laser light source to a laser irradiation region and the size of the laser irradiation region. The laser radiation unit 8 emits laser light in such a manner that the laser light progressively converges in the form of an inverted cone. Accordingly, if the welding section is located near the laser radiation unit 8, the laser irradiation region is large, and the laser irradiation region becomes smaller in area with increasing distance from the laser radiation unit 8. It will be understood from FIG. 5 that the laser irradiation region is large ($A_0$) at a distance of $Z_0$ from the laser radiation unit 8 and becomes progressively smaller ($A_1$, $A_2$) with increasing distance ($Z_1$, $Z_2$) from the laser radiation unit 8.

Figure 6A:
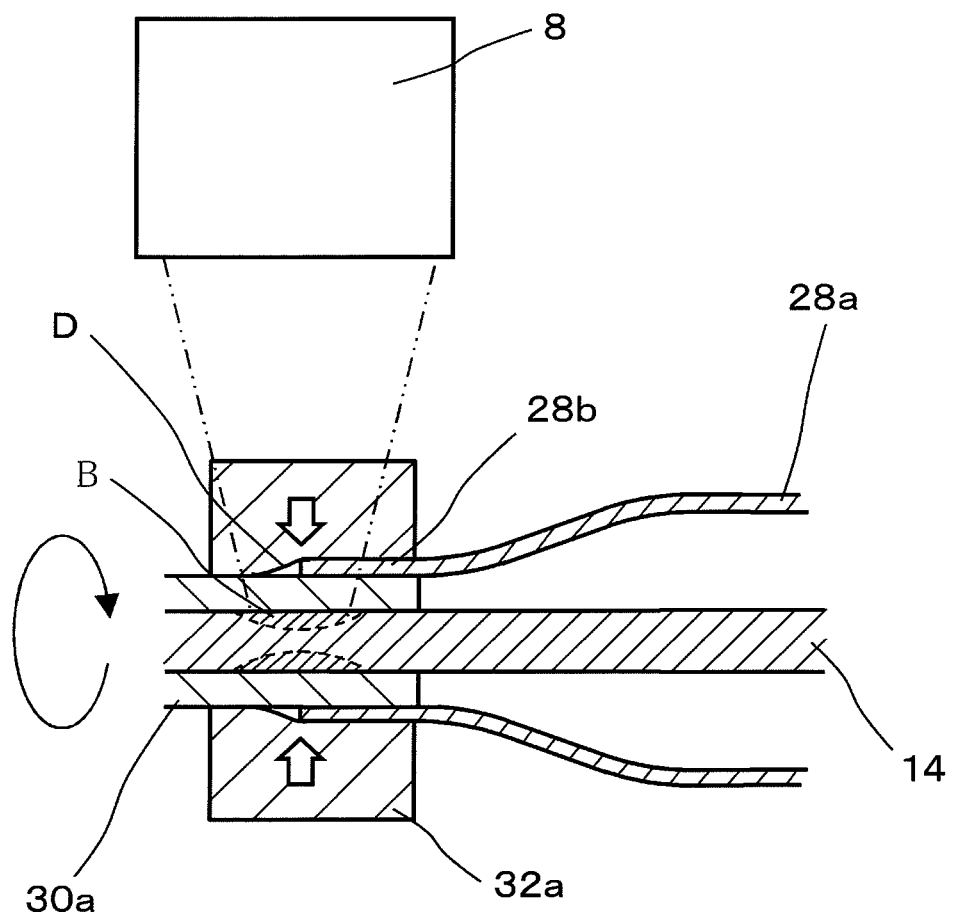
FIG. 6A is a sectional view of a welding section of the balloon catheter before welding.
Figure 6B:
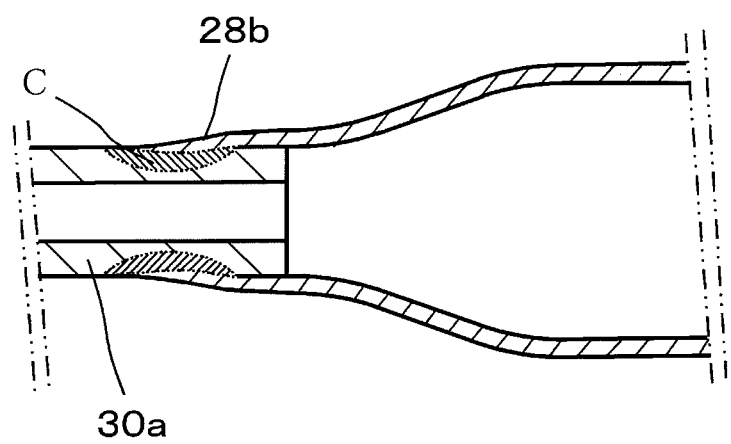
FIG. 6B is a sectional view of a welded section of the balloon catheter after the welding.

FIGS. 6A and 6B are sectional views respectively illustrating the welding section of the balloon catheter before welding and the welded section of the balloon catheter after the welding. The welding method will be explained with reference to FIGS. 6A and 6B in addition to FIGS. 4 and 5.

In this embodiment, the end portion 28b at one end of the balloon 28 is welded first, as illustrated in FIG. 4, and then the other end portion 28c is welded.

First, the welding start position is set with respect to each of the one end portion and the other end portion of the balloon 28. Specifically, the operator manipulates the welding manipulator 6 while confirming the position of the balloon catheter 26 on the camera-acquired image displayed on the monitor 4, and determines an appropriate welding start position. In this embodiment, the tip positions of the one and other end portions of the balloon 28 are set as the welding start positions and registered in a memory (storage) 25. Radiation of the laser light is started at the welding start position, and therefore, the welding start position is the laser light radiation start position. Likewise, radiation of the laser light is terminated at the welding end position, and thus the welding end position is the laser light radiation end position.

After the welding start positions are determined, the position and laser output of the laser radiation unit 8 along the Z-axis direction are set with respect to each of the one and other end portions of the balloon 28. In this case, the laser output may be varied in accordance with the degree of progress of the welding, and in this embodiment, the laser output is set so as to gradually lower as the welding advances, for example. The position of the laser radiation unit 8 along the Z-axis direction is stored in the memory 25 as one of the welding parameters.

After the welding-related condition is set in this manner, the welding start button of the welding manipulator 6 is pressed with the cover 2 closed, whereupon the welding starts under the set condition with the various devices controlled by the welding controller 24.

As soon as the welding is started under the set condition, the chuck 16 rotates the shaft 14 as illustrated in FIG. 6A, so that the catheter tubes 30a and 30b, the balloon 28, and the pressure tubes 32a and 32b rotate together with the shaft 14. In FIGS. 6A, 6B and like figures, the thickness of the balloon 28 and of the catheter tube 30a is exaggerated for ease of illustration. For example, the balloon catheter is illustrated in FIG. 6A in a manner such that there is a substantial difference in level between the tip of the end portion 28b of the balloon and the catheter tube 30a, but in practice, the level difference is very small.

Subsequently, laser light is emitted from the laser radiation unit 8. The laser light thus emitted penetrates through the pressure tube 32a, the end portion 28b of the balloon and the catheter tube 30a and reaches the shaft 14. The shaft 14 generates heat when irradiated with the laser light. The heat transfers from a heated portion B of the shaft 14 to the catheter tube 30a, thus heating the catheter tube 30a, and then from the heated catheter tube 30a to the end portion 28b of the balloon, thus heating the end portion 28b.

In the sectional view of FIG. 6B illustrating the welded section of the balloon catheter, a fused portion C is indicated by narrow hatching (thin slanting lines). The catheter tube 30a and the end portion 28b of the balloon are heated from their radially inward side and, on reaching the melting point, are fused together. The catheter tube 30a and the end portion 28*b* of the balloon are applied with pressure toward the axis by the pressure tube 32*a*, and accordingly, when the catheter tube 30*a* and the end portion 28*b* are melted and thus have fluidity, the melt of the end portion 28*b* flows along the surface of the catheter tube 30*a* radially inward into the space (D in FIG. 6A) located ahead of the end portion 28*b* and between the pressure tube 32*a* and the catheter tube 30*a*, and fuses with the catheter tube 30*a*.

Figure 7A:
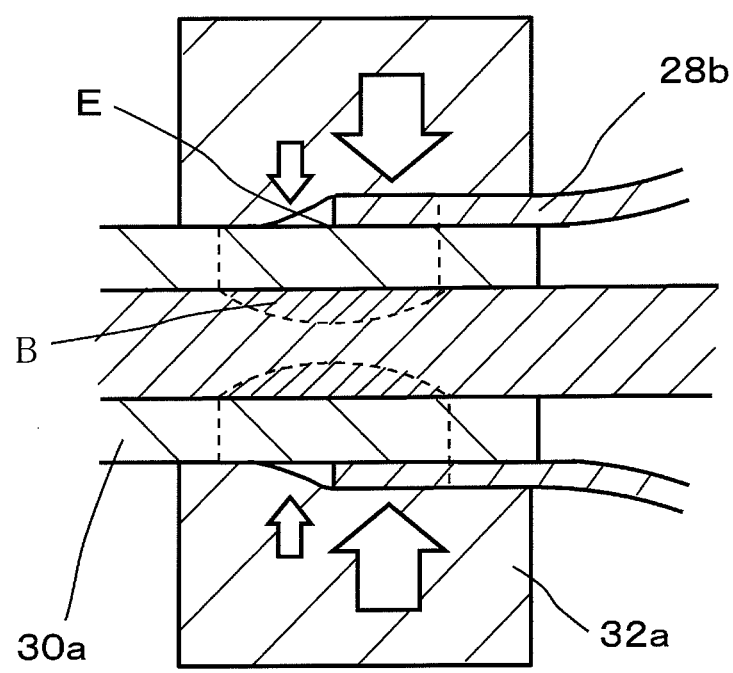
FIG. 7A is a sectional view of the welding section of the balloon catheter before the welding.
Figure 7B:
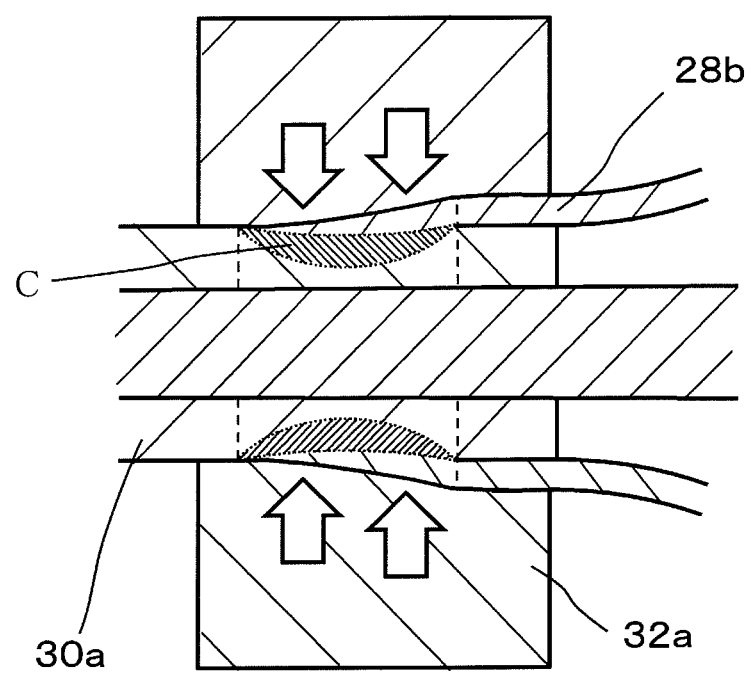
FIG. 7B is a sectional view of the welded section of the balloon catheter after the welding.

This process will be explained in more detail with reference to FIGS. 7A and 7B. The pressure tube 32*a* applies pressure onto both regions of the balloon catheter, that is, a single-layer region where only the catheter tube 30*a* exists and a double-layer region where the end portion 28*b* of the balloon is lapped over the outside of the catheter tube 30*a*. As illustrated in FIG. 7A, the thickness of the single-layer region where the catheter tube 30*a* alone exists differs from that of the double-layer region where the end portion 28*b* of the balloon is lapped over the catheter tube 30*a*, and therefore, before the heating, there is a pressure difference between the single-layer region and the double-layer region with a boundary coinciding with a level difference point E, as indicated by hollow arrows with different widths in FIG. 7A. When the catheter tube 30*a* and the end portion 28*b* of the balloon are heated to their melting point and come to have fluidity, the level difference disappears because the force of maintaining the level difference is lost, with the result that the joint between the end portion 28*b* of the balloon and the catheter tube 30*a* turns into a smoothly curved surface without any level difference or unevenness, as illustrated in FIG. 7B.

The laser radiation unit 8 emits the laser light for the set time with the laser output varied as previously set, whereupon the welding of the one end portion of the balloon is completed. The laser radiation unit 8 is then moved to the welding start position of the other end portion of the balloon, and the other end portion is subjected to the welding under the set condition in the same manner as the one end portion.

After the welding of the one and other end portions of the balloon 28 is completed, the shaft 14 is detached from the chuck 16, and the pressure tubes 32*a* and 32*b* and the shaft 14 are removed, whereby the finished balloon catheter 26 is obtained.

The balloon catheter 28 obtained in this manner by welding the end portions 28*b* and 28*c* of the balloon to the respective catheter tubes 30*a* and 30*b* has a shape such that, as illustrated in FIG. 6B, the outer diameter at the tip of the end portion 28*b* of the balloon is equal to that of the catheter tube 30*a* and smoothly increases toward the body of the balloon.

As described above, with the balloon catheter manufacturing apparatus 1 and the manufacturing method, the laser light penetrates through the balloon 28 and the catheter tube 30*a*, 30*b* and heats the shaft 14 so that the catheter tube 30*a*, 30*b* may be heated from the radially inward side, whereby the welding can be carried out while preventing excessive heating of the balloon 28, which is smaller in thickness than the catheter tube 30*a*, 30*b*, and thereby preventing breakage or the like of the balloon 28.

Also, the catheter tube 30*a*, 30*b* is heated from its radially inward side while being applied with pressure toward the axis by the pressure tube 32*a*, 32*b* which is an elastic member, and accordingly, the balloon 28 is fused into and bonded to the catheter tube 30*a*, 30*b*. The pressure tube 32*a*, 32*b* utilizes its elastic force, and not heat shrinkage or the like, to apply pressure, and therefore, the pressure application position is not displaced or an awkward situation where it is difficult to remove the pressure tubes 32*a* and 32*b* after the welding does not occur. Consequently, the welding section can be applied with pressure uniformly and welded without any unevenness remaining on the welded surface.

In FIG. 6A, the laser radiation unit 8 is fixed in the Z-axis direction at a location near the shaft 14, to emit the laser light onto a relatively large laser irradiation region. The laser radiation unit 8 is fixed, but since the shaft 14 is rotated while being held by the chuck 16, the central portion of the laser irradiation region on the outer peripheral surface of the shaft 14 is heated most, with the outward portions less heated. The end portion 28*b*, 28*c* of the balloon 28, which is located at the center of the laser irradiation region, is applied with pressure by the corresponding pressure tube 32*a*, and accordingly, the end portion of the balloon is fused into the catheter tube 30*a* as if it were buried in the catheter tube 30*a*. As a result, the end portion 28*b* of the balloon 28 and the catheter tube 30*a* are welded together, leaving a smooth surface without unevenness.

Further, after the one end portion of the balloon 28 is welded, the welding of the other end portion can be immediately executed, making it possible to improve the productivity of the balloon catheter 26.

Embodiment 2

In Embodiment 1 described above, the position of the laser radiation unit 8 in the X-axis direction is fixed, and accordingly, a remoter portion of the shaft 14 from the center of the laser irradiation region is less heated, so that the extent to which the end portion 28*b* of the balloon is fused is smaller at the remoter portion. Because of this, the end portion 28*b* of the balloon is fused locally at the center of the laser irradiation region. In Embodiment 2 of the present invention, the laser radiation unit 8 is moved in the X- and Z-axis directions and the output of the laser light is variably set so that the welding can be carried out under a condition suited to the welding object.

Figure 8A:
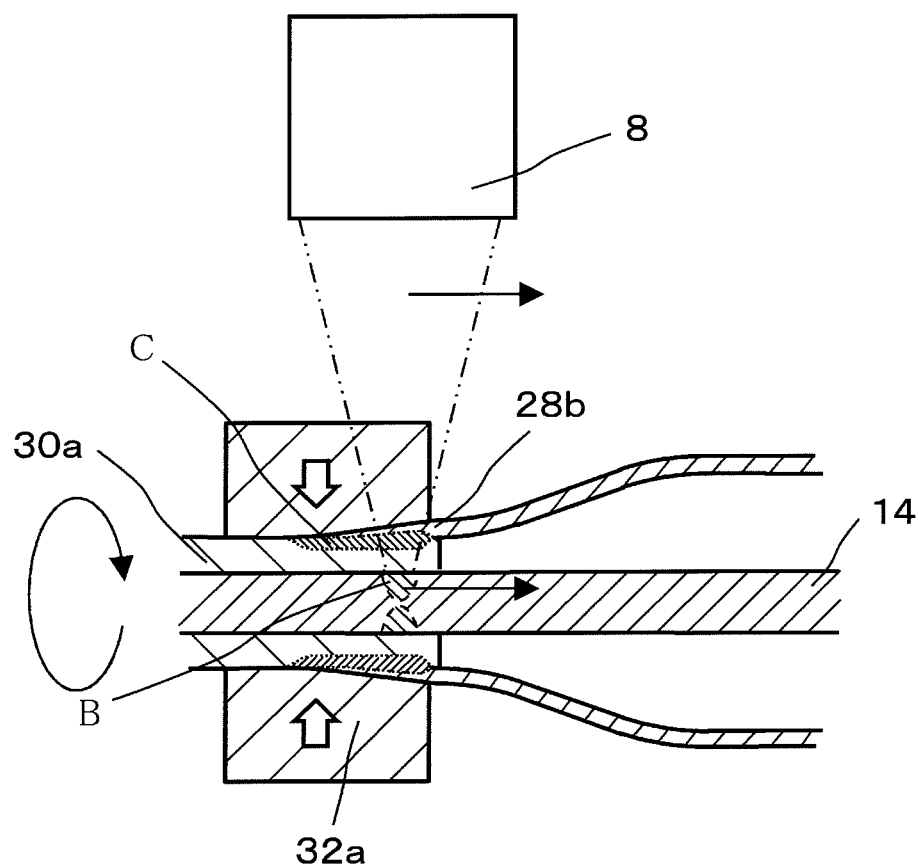
FIG. 8A is a sectional view of the welded section of the balloon catheter before the welding is completed.
Figure 8B:
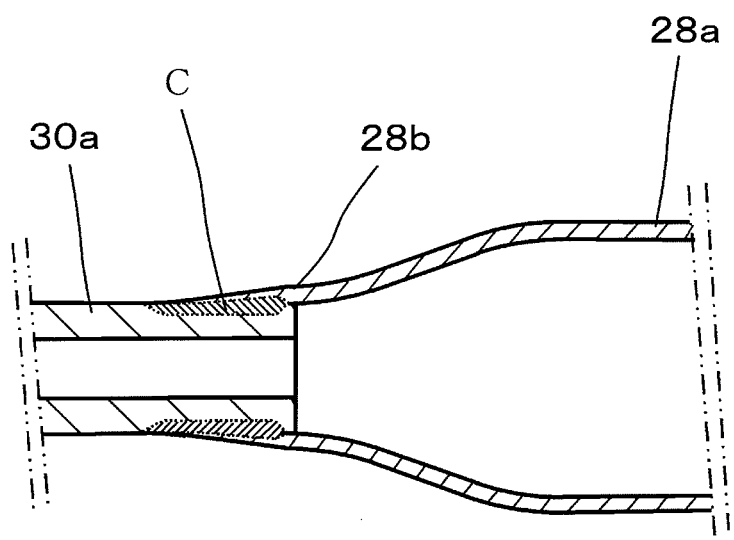
FIG. 8B is a sectional view of the welded section of the balloon catheter after the welding is completed.

As illustrated in FIG. 8A, the position of the laser radiation unit 8 along the Z axis is fixed so as to be remoter from the shaft 14 than in the case of Embodiment 1 such that a narrower part of the laser light impinges on the shaft 14 to form a smaller laser irradiation region, and also the laser radiation unit 8 is moved along the X axis with the laser output lowered. As the laser irradiation region moves, the heated portion B moves along the X axis, and also the fused portion C of the balloon 28 and the catheter tube 30*a* moves along the X axis. The laser output is lowered as the laser irradiation region moves. Consequently, the fused portion C spreads in the X-axis direction, and as will be seen from FIG. 8B in comparison with FIG. 6B, the end portion 28*b* of the balloon is fused into the catheter tube 30*a* over a wider range as if it were buried in the catheter tube 30*a*, with the result that the end portion 28*b* and the catheter tube 30*a* are welded together leaving a smooth surface free of unevenness.

Accordingly, the joint between the end portion of the balloon and the catheter tube can be formed into a desired surface profile suited for use, making it possible to manufacture the balloon catheter 26 well suited for medical use.

Figure 9:
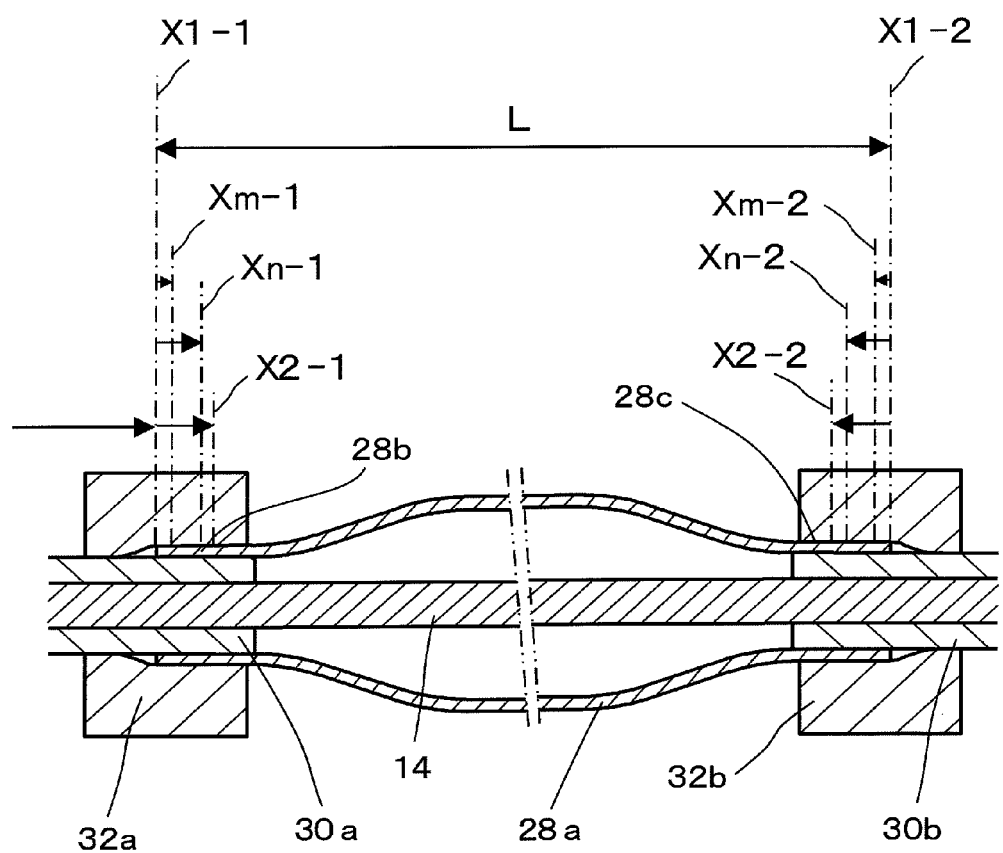
FIG. 9 is a sectional view illustrating laser light radiation start and end positions of the balloon catheter.

FIG. 9 is a sectional view of the balloon and the catheter tubes, which are objects to be welded together, and illustrates the positions for starting and ending radiation of the laser light from the laser light source onto the balloon catheter. Specifically, FIG. 9 illustrates the positional relationship among a laser light radiation start position (X1-1) where the laser radiation unit 8 as the laser light source starts to emit the laser light, a laser light radiation end position (X2-1) where the radiation of the laser light is ended, a laser light radiation start position (X1-2) which is spaced at a distance (L) from the laser light radiation start position (X1-1) and at which radiation of the laser light to the other end portion of the balloon is started, and a laser light radiation end position (X2-2) where the radiation of the laser light is terminated.

In this embodiment in particular, the welding is effected such that the output of the laser light is set high at the tip of each end portion of the balloon 28 and is lowered with distance toward the center, that is, the body, of the balloon 28, and accordingly, the extent to which the shaft 14 is heated, and thus the extent to which the end portion 28b, 28c of the balloon is fused become smaller with distance toward the balloon body. It is therefore possible to obtain the joined balloon catheter 26 having a shape such that the outer diameter at the tip of each end portion of the balloon 28 is equal to that of the catheter tube 30a, 30b and smoothly increases toward the balloon body.

The laser light radiation start and end positions are registered in the memory 25 as a storage. When the welding is to be executed, the laser light radiation start and end positions are read from the memory 25 by the welding controller 24, which functions also as a position registration-readout unit, and using the laser supporting unit, radiation of the laser light is continued from the laser light radiation start position to the laser light radiation end position, to weld the welding sections where the end portions of the balloon 28 are lapped over the respective catheter tubes 30a and 30b.

As illustrated in FIG. 9, predetermined positions (Xm-1) and (Xn-1) may be set between the laser light radiation start and end positions (X1-1) and (X2-1), and a welding condition such as the laser radiation condition may be set with respect to each of the predetermined positions and registered in the memory 25. When the welding is to be executed, the registered welding conditions may be read from the memory 25 by the welding controller 24 so that the welding section may be subjected to welding under the welding conditions thus read out, as described in detail later with reference to FIGS. 15 and 16.

FIG. 10 illustrates a data structure of the welding conditions for the balloon catheter, stored in the memory 25. Specifically, FIG. 10 exemplifies, as welding parameters of the welding conditions, (1) diameter of the laser light irradiation region (laser spot), (2) rotating speed of the shaft 14, (3) whether the laser radiation unit 8 is fixed or moved, (4) laser light radiation start position, (5) laser light radiation end position, (6) moving speed of the laser radiation unit 8, (7) whether one side or both sides of the balloon 28 are to be welded, (8) distance over which the laser radiation unit 8 is to be moved where both sides of the balloon 28 need to be welded, (9) material of the balloon 28 and the catheter tubes 30a and 30b, and (10) thickness of the balloon and the catheter tubes. These items constitute a single welding condition, and a plurality of welding conditions are stored in the memory 25.

In the example illustrated in FIG. 10, an evaluation score obtained by actually performing the welding is stored with respect to each welding condition. Namely, balloon catheters are actually welded with the welding parameters varied to obtain a desired balloon catheter 26, then the balloon catheters obtained are evaluated, and the evaluation results are stored in a manner associated with the respective welding conditions. Subsequently, the welding conditions are sorted and displayed in order of the evaluation score so that an optimum welding condition can be easily located. Also, an experimental design method, for example, may be employed so that when an evaluation result obtained by actually performing the welding with the welding parameters varied is input, candidates for an optimum welding condition for obtaining a desired balloon catheter 26 may be presented.

Figure 11:
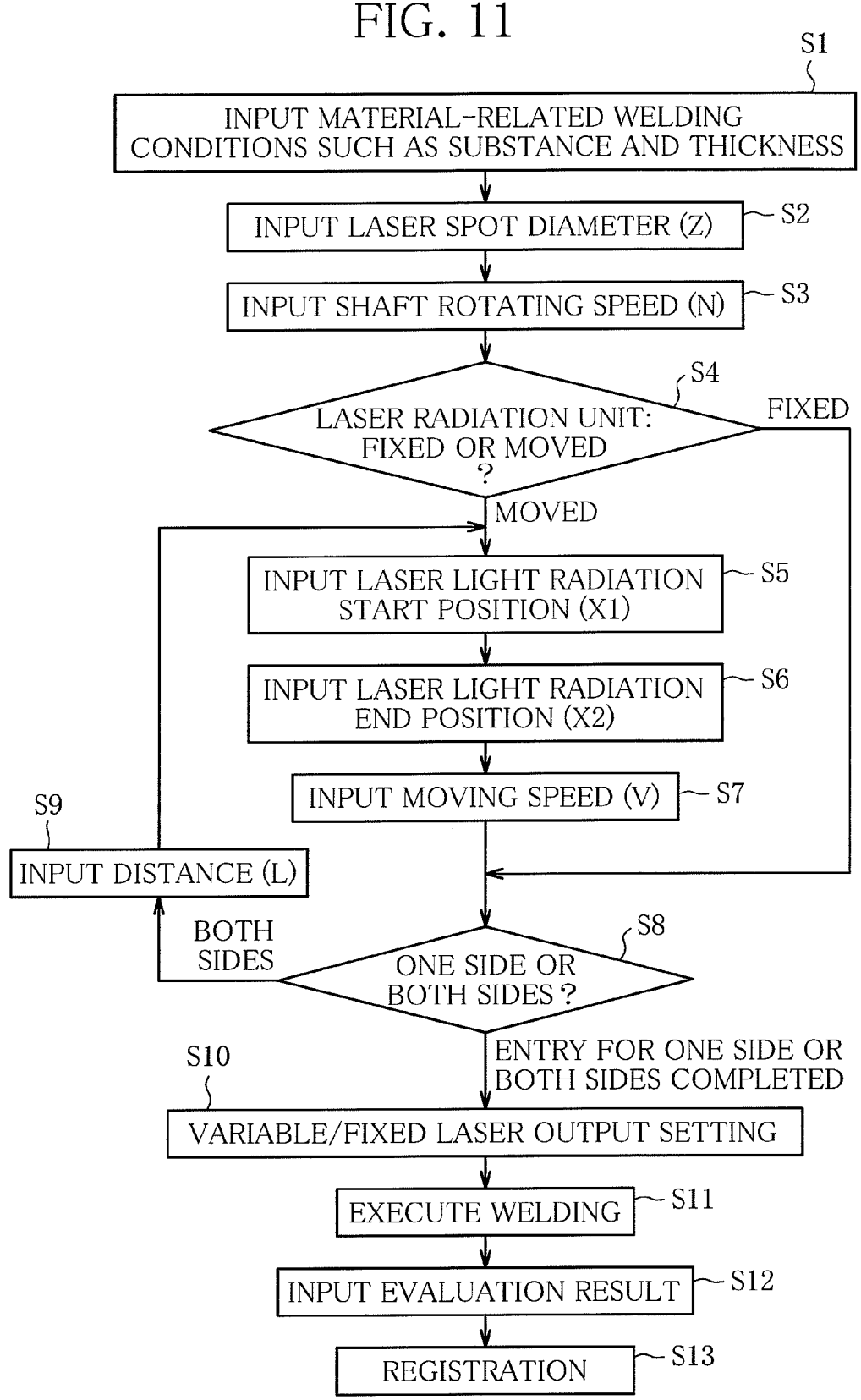
FIG. 11 is a flowchart illustrating a procedure for registering the welding condition in the memory 25.

FIG. 11 is a flowchart illustrating a procedure for registering the welding condition in the memory 25. Referring to the procedure illustrated in the flowchart, the operation of registering the welding condition will be explained. First, conditions related to the balloon 28 and the catheter tubes 30a and 30b, such as the material and the thickness, are input (Step S1).

Subsequently, the laser spot diameter is input (Step S2), followed by the entry of the rotating speed of the shaft 14 (Step S3). Then, whether the laser radiation unit 8 is to be fixed or moved is entered (Step S4). Where the laser radiation unit 8 is to be moved, the laser light radiation start position (Step S5), the laser light radiation end position (Step S6) and the moving speed of the laser radiation unit 8 (Step S7) are input. On the other hand, where the laser radiation unit 8 is to be fixed, Steps S5, S6 and S7 are not executed.

Then, whether the part of the balloon 28 to be welded is one end portion only or both end portions is input (Step S8). Where the both end portions 28b and 28c of the balloon 28 are to be welded, the distance over which the laser radiation unit 8 is to be moved is input (Step S9), followed by the entry of the laser light radiation start position (Step S5) and laser light radiation end position (Step S6) for the other end portion and the moving speed (Step S7). After the entry of the items with respect to only one or both end portions of the balloon 28 is completed, whether the laser output is to be varied or not is set. Where the laser output is to be varied, the manner of how the laser output is varied is input (Step S10). Subsequently, the balloon is actually welded (Step S11), and the result of evaluation of the welding is entered (Step S12). The items entered as stated above are registered as a single welding condition in the memory 25 (Step S13).

Figure 12:
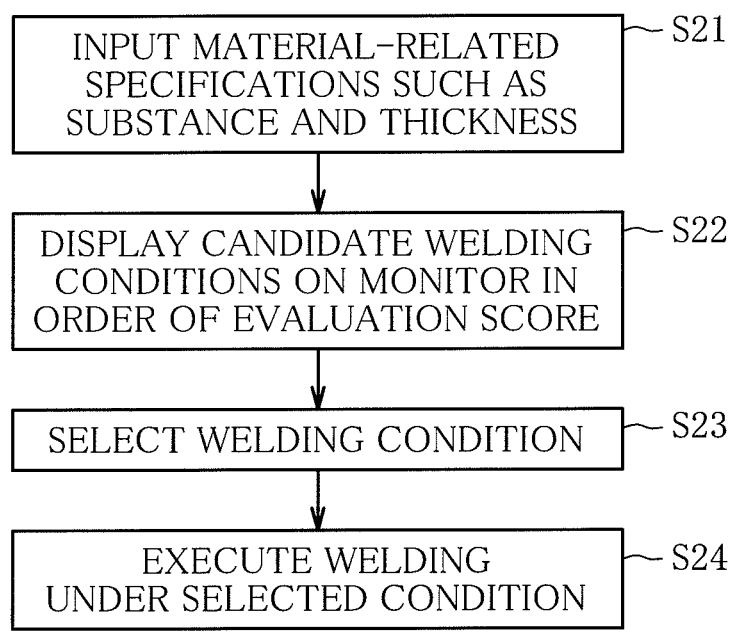
FIG. 12 is a flowchart illustrating a procedure for reading out the welding conditions registered in the memory and executing a welding operation.

FIG. 12 is a flowchart illustrating a procedure for reading out a welding condition registered in the memory 25 and executing the welding. First, specifications relating to the welding, such as the material and thickness of the balloon 28 and the catheter tubes 30a and 30b, are input (Step S21), whereupon the welding conditions identical or similar to the input specifications are displayed on the monitor 4 in descending order of the evaluation score obtained by actually executing the welding (Step S22). A desired welding condition is selected from among those displayed on the monitor (Step S23), whereby the welding can be executed under the selected condition (Step S24). If an additional welding condition is needed, any desired welding condition may be modified by changing one or more of the welding parameters, and the welding condition thus modified may be registered in the memory 25 so that the welding can be executed under the new condition. If the welding result obtained is better than the already registered one, then it means that a more desirable welding condition could be obtained.

The balloon catheter manufacturing apparatus of the present invention stores not only a plurality of welding conditions each including a set of welding parameters but also evaluation results obtained by actually performing the welding under the respective welding conditions. Thus, by just selecting a welding condition associated with a high evaluation score, it is possible to stably perform a high-quality welding operation. That is to say, the balloon catheter manufacturing apparatus is instructed (taught) the welding conditions and the evaluation results. As soon as welding-related specifications such as the material and thickness of a desired balloon and catheter tubes are input, welding conditions matching the input specifications and associated with good evaluation results are displayed as candidate welding conditions on the monitor, thus providing the advantage that the operator can quickly select a desired welding condition from among the candidate welding conditions already evaluated.

Figure 13:
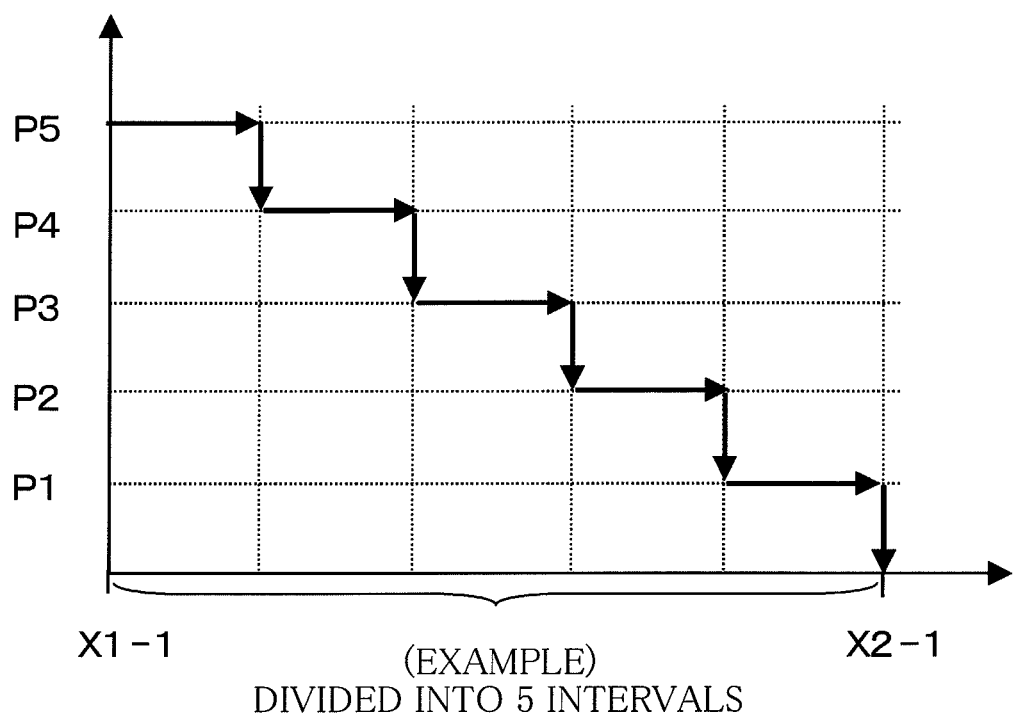
FIG. 13 illustrates an example of varying a laser output in a step-by-step manner from the laser light radiation start position to the laser light radiation end position.
Figure 14:
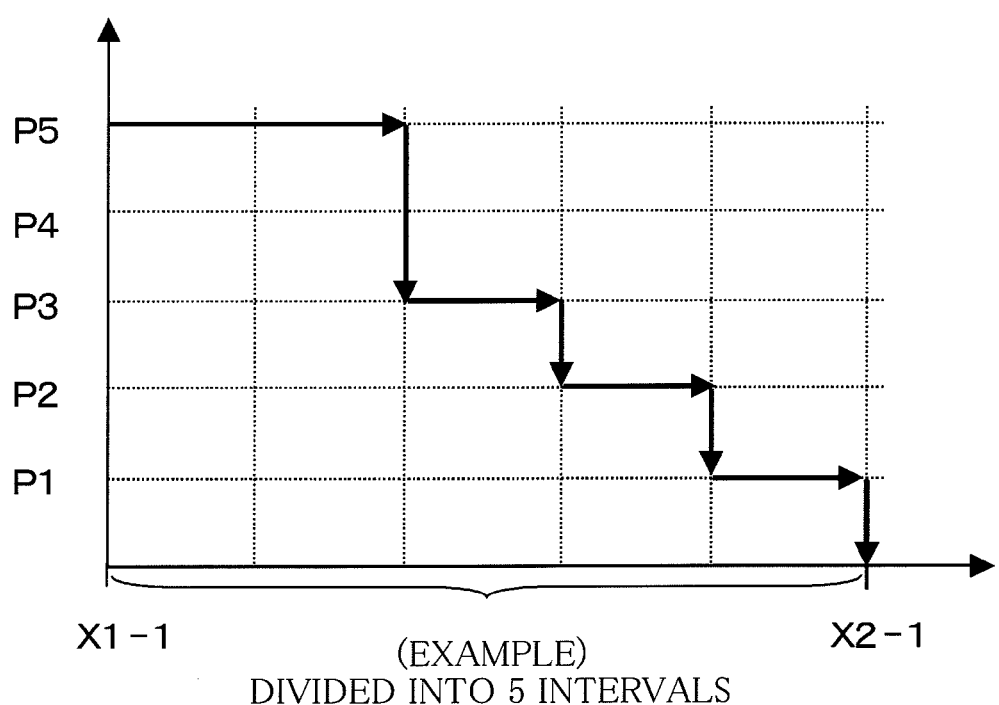
FIG. 14 illustrates another example of varying the laser output in a step-by-step manner from the laser light radiation start position to the laser light radiation end position.

According to the present invention, the laser output of the laser radiation unit can be variably set as stated above, though such a parameter is not listed in the welding parameters illustrated in FIG. 10. FIGS. 13 and 14 each illustrate an example of varying the laser output in stages during the movement from the welding start position to the welding end position. In the example illustrated in FIG. 13, the distance between the laser light radiation start position (X1-1), which is the welding start position, and the laser light radiation end position (X2-1), which is the welding end position, is divided into five equal intervals, and the laser output is decreased step by step in five stages. In the example illustrated in FIG. 14, the distance between the laser light radiation start position (X1-1) and the laser light radiation end position (X2-1) is similarly divided into five equal intervals, and the laser output is kept at a maximum output in the first two of the five intervals and is thereafter decreased in stages.

Where the laser output is set at the maximum output at the welding start position and is decreased step by step thereafter as illustrated in FIGS. 13 and 14, the tip (portion near the end face) of the balloon can be welded to the catheter tube as if it were buried in the catheter tube, and the extent to which the balloon is buried in the catheter tube can be gradually reduced with distance from the tip of the balloon. Consequently, the balloon and the catheter tube can be bonded together in such a manner that the surface of the balloon smoothly connects to that of the catheter tube without unevenness.

In this manner, according to the present invention, predetermined positions between the laser light radiation start and end positions and welding conditions applied to the respective predetermined positions are registered in the storage (memory 25). When the welding is to be executed, the registered welding conditions are read from the storage by the welding control unit (welding controller 24), and the welding section is welded under the read welding conditions.

Figure 15:
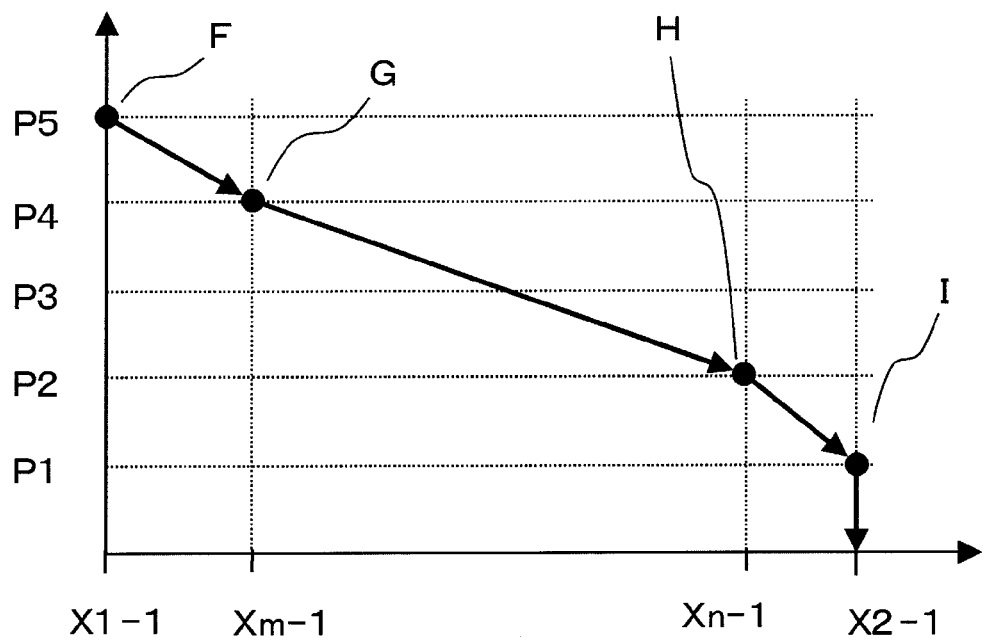
FIG. 15 illustrates an example of varying the laser output continuously from the laser light radiation start position to the laser light radiation end position via predetermined positions Xm-1 and Xn-1.

In the above examples, the distance between the laser light radiation start position (X1-1) and the laser light radiation end position (X2-1) is divided into five intervals but may alternatively be divided into three or two intervals or into a desired number of intervals. Also, instead of varying the laser output step by step, the laser output may be set so as to vary continuously or in an analog manner to a desired value. For example, as illustrated in FIG. 15, the welding condition may be set with respect to each of predetermined positions (Xm-1, Xn-1) between the laser light radiation start position (X1-1), which is the welding start position, and the laser light radiation end position (X2-1), which is the welding end position. In this case, as the laser radiation unit 8 passes through the predetermined positions, the laser output is continuously and linearly varied from point F to point I via points G and H, as illustrated in FIG. 15.

Figure 16:
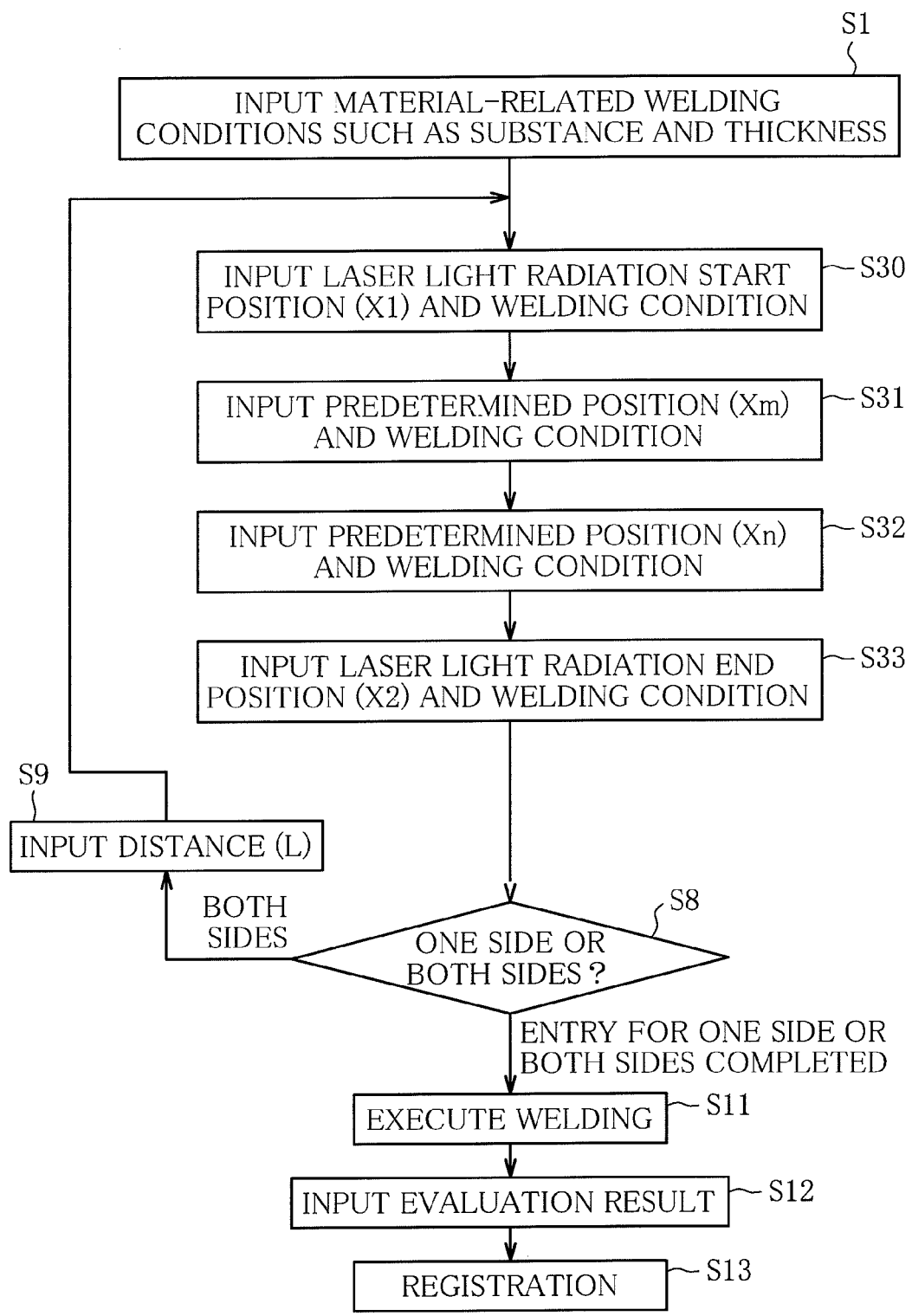
FIG. 16 is a flowchart illustrating a procedure for registering the welding conditions for the laser light radiation start position, the predetermined positions Xm-1 and Xn-1, and the laser light radiation end position.

FIG. 16 is a flowchart illustrating a procedure for setting the welding conditions in the manner illustrated in FIG. 15. In the procedure illustrated in FIG. 16, first, conditions such as the material and thickness of the balloon 28 and the catheter tubes 30a and 30b are input, as in Step S1 illustrated in FIG. 11. Then, in Step S30, the laser light radiation start position (X1-1) and the welding condition applied to this position, for example, a laser output (P5), are input. Subsequently, the welding condition applied to the predetermined position (Xm-1), for example, a laser output (P4), is input in Step S31, then the welding condition applied to the predetermined position (Xn-1), for example, a laser output (P2), is input in Step S32, and the laser light radiation end position (X2-1) and the welding condition applied to this position, for example, a laser output (P1), are input in Step S33. By setting the conditions in this manner, it is possible to vary the laser output in the manner illustrated in FIG. 15 as the laser radiation unit moves. Where similar welding conditions are to be set with respect to both end portions of the balloon catheter, Step S9 is executed and the flow of FIG. 16 returns to Step S30. The welding conditions for the other end portion of the balloon catheter are entered in the same manner as explained above with reference to FIG. 11. In FIG. 16, like step numbers are used to denote like steps also appearing in FIG. 11, and description of such steps is omitted.

Thus, the balloon catheter 26 has such a shape that the end portions 28b and 28c of the balloon smoothly connect to the respective catheter tubes 30a and 30b via the joints having no level difference or unevenness. The balloon catheter, when used as a medical instrument, can therefore be safely inserted into the body via a blood vessel or the like without damaging the surrounding tissue, thus ensuring safe medical treatment.

While the balloon catheter and balloon catheter manufacturing apparatus and method according to the present invention have been described above with reference to Embodiments 1 and 2, it is to be noted that the present invention is not limited to the foregoing embodiments.

Figure 17:
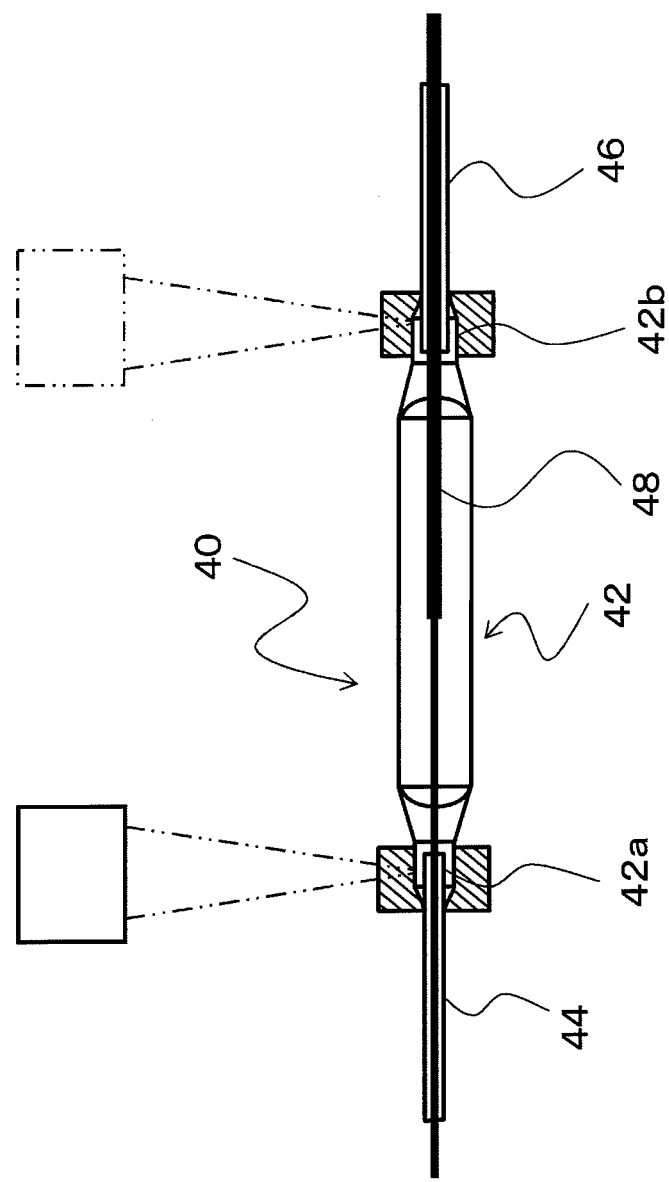
FIG. 17 schematically illustrates a first modification of the balloon catheter.

FIG. 17 illustrates a first modification of the balloon catheter 26 by way of example. As illustrated in FIG. 17, a balloon catheter 40 according to the first modification includes a balloon 42 having opposite end portions 42a and 42b, and first and second catheter tubes 44 and 46 having different diameters and inserted into the respective end portions 42a and 42b.

When welding the catheter tubes 44 and 46 with different diameters to the respective end portions 42a and 42b of the balloon, a dual-diameter shaft 48 of which the diameter varies in the middle so as to correspond to the inner diameters of the respective catheter tubes 44 and 46 is used. The shaft 48 is inserted through the balloon with its diameters associated with the corresponding catheter tubes 44 and 46 with different diameters. Thus, also in the case of welding the catheter tubes 44 and 46 with different diameters, the one and other end portions 42a and 42b of the balloon 42 can be successively welded, providing the same advantageous effects as those achieved by the foregoing embodiments.

Figure 18:
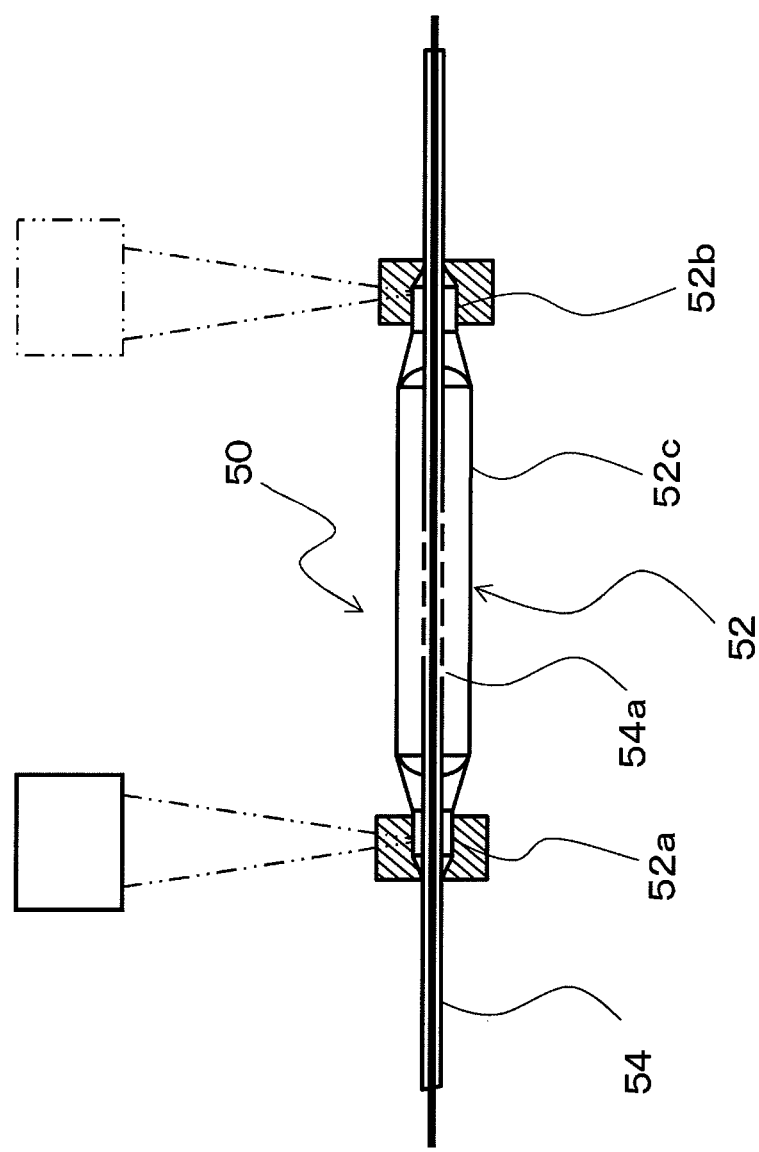
FIG. 18 schematically illustrates a second modification of the balloon catheter.

FIG. 18 illustrates a second modification of the balloon catheter 26. As illustrated in the figure, a balloon catheter 50 is constituted by a balloon 52 and a single catheter tube 54 inserted through the balloon 52 past opposite end portions 52a and 52b. A plurality of holes 54a are formed in that portion of the catheter tube 54 which corresponds in position to a body 52c of the balloon 52, to allow a fluid medical agent or the like to be supplied to the interior of the balloon 52.

Also in the case of the balloon catheter 50 constructed as stated above, the end portions 52a and 52b of the balloon and the catheter tube 54 can be welded together by the balloon catheter manufacturing apparatus 1 in the same manner as described above with reference to the above embodiments. Thus, the same advantageous effects as those obtained by the foregoing embodiments can be achieved.

The balloon catheters of the foregoing embodiments are configured to be inserted into a blood vessel. Alternatively, the balloon catheter may be configured to be inserted into the body cavity such as the chest cavity or abdominal cavity, or other lumens such as the alimentary canal or ureter.

In the aforementioned Embodiments 1 and 2 of the present invention, an inflatable balloon is welded to a distal end portion of a hollow soft catheter tube. The present invention can also be applied to the welding of hollow soft catheter tubes to each other.

Embodiment 3

In the following, Embodiment 3 of the present invention will be described. Catheter tubes (hereinafter abbreviated as catheters) generally used have a variety of diameters ranging from about 1 mm to 10 mm and a variety of lengths ranging from several centimeters to about 2 m depending on applications. Catheters currently used include those having different diameters and obtained by connecting a small-diameter catheter to a large-diameter catheter. When the catheters with different diameters are connected to each other, the joint needs to be formed so as to have a smooth surface profile, in order that the tissue in the body may not be damaged, as in the case of the balloon catheter. According to the present invention, the joint of the catheters can be formed into a desired surface profile matching application. It is therefore possible to manufacture catheters suited for medical use.

Figure 19A:
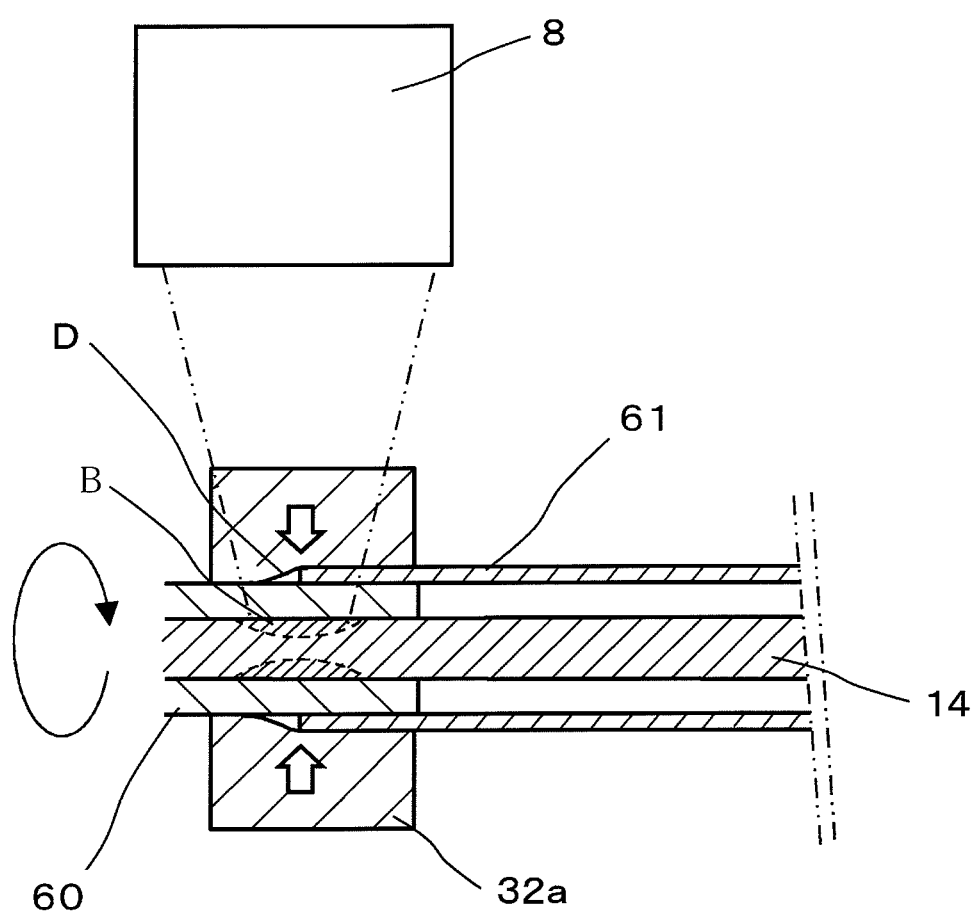
FIG. 19A is a sectional view of a welding section of a pair of catheters with different diameters before the welding.
Figure 19B:
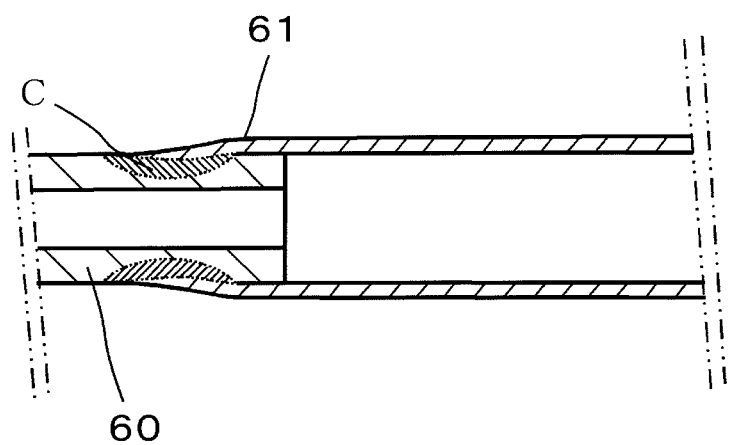
FIG. 19B is a sectional view of a welded section of the pair of catheters with different diameters after the welding.

FIG. 19A is a sectional view of a welding section where an end portion of a large-diameter catheter is fitted on an end portion of a small-diameter catheter before welding is executed by irradiating the welding section with laser light, and FIG. 19B is a sectional view of a welded section obtained by the welding to provide a catheter having its diameter varied in the middle.

As illustrated in FIG. 19A, an inner-side tube 60 as a small-diameter catheter having an inner diameter nearly equal to the diameter of the shaft 14 is fitted around the shaft 14, then an end portion of an outer-side tube 61 as a large-diameter catheter having an inner diameter nearly equal to the outer diameter of the inner-side tube 60 and having a thickness smaller than that of the inner-side tube 60 is fitted on an end portion of the inner-side tube 60, and the pressure tube 32a is fitted around the outer- and inner-side tubes 61 and 60 including the end of the outer-side tube 61. Then, the joint, or the welding section, is irradiated with the laser light from the laser radiation unit 8. As regards the welding section, the outer-side tube 61 with a fixed diameter, illustrated in FIG. 19A, can be regarded as equivalent to the balloon 28 in FIG. 6A already explained. The laser light emitted from the laser radiation unit 8 penetrates through the pressure tube 32a and the outer- and inner-side tubes 61 and 60 and reaches the shaft 14. The shaft 14 generates heat when irradiated with the laser light. The inner-side tube 60 is heated by the heat from the heated portion B of the shaft 14, and the outer-side tube 61 is heated by the heat from the thus-heated inner-side tube 60.

In the sectional view of FIG. 19B, a fused portion C is indicated by narrow hatching (thin slanting lines). The inner- and outer-side tubes 60 and 61 are heated from their radially inward side and, on reaching the melting point, are fused together. The inner- and outer-side tubes 60 and 61 are applied with pressure toward the axis by the pressure tube 32a, and accordingly, when the inner- and outer-side tubes are melted and thus have fluidity, the molten end portion of the outer-side tube flows into a space (space D) located between the pressure tube 32a and the outer-side tube 61, and becomes fused with the inner-side tube. Thus, the joint between the outer- and inner-side tubes 61 and 60 is formed into a shape such that the outer diameter at the tip of the outer-side tube 61 is equal to that of the inner-side tube 60 and progressively increases toward the remaining portion of the outer-side tube 61.

Figure 20A:
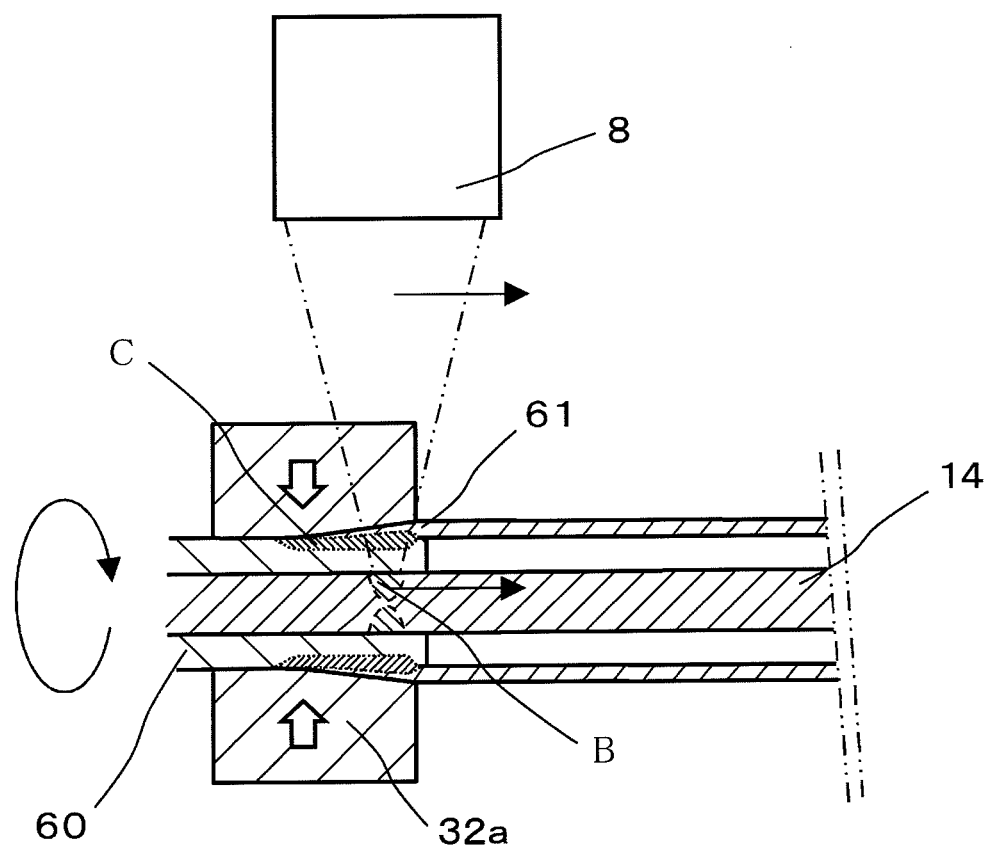
FIG. 20A is a sectional view of the welded section of the pair of catheters with different diameters before the welding is completed.
Figure 20B:
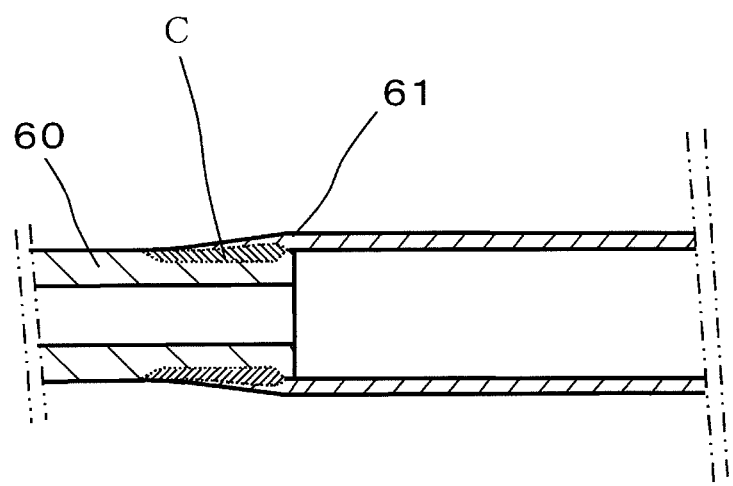
FIG. 20B is a sectional view of the welded section of the pair of catheters with different diameters after the welding is completed.

FIGS. 20A and 20B illustrate a case where, with the position of the laser radiation unit 8 along the Z axis fixed so as to be somewhat remoter from the shaft 14 than in the case of FIG. 19A to use a narrower part of the laser light to obtain a smaller laser irradiation region, the laser radiation unit 8 is moved along the X axis while lowering the laser output. As the laser irradiation region moves as illustrated in FIG. 20A, the heated portion B moves along the X axis, and also the fused portion C of the outer- and inner-side tubes 61 and 60 moves along the X axis. At this time, the laser output is lowered as the laser irradiation region moves. Consequently, the fused portion C spreads in the X-axis direction, and as will be clear from FIG. 20B in comparison with FIG. 19B, the end portion of the outer-side tube 61 is fused with the inner-side tube 60 over a wider range as if it were buried in the inner-side tube 60, thus providing a smooth joint without unevenness.

In the above Embodiment 3 of the present invention, the welding section is constituted by overlapped end portions of a pair of catheters with different diameters and is welded together using the laser.

Embodiment 4

The present invention can also be applied to the welding of mutually butted end faces of a pair of catheters. The manner of how the welding is executed will be described below as Embodiment 4.

Figure 21A:
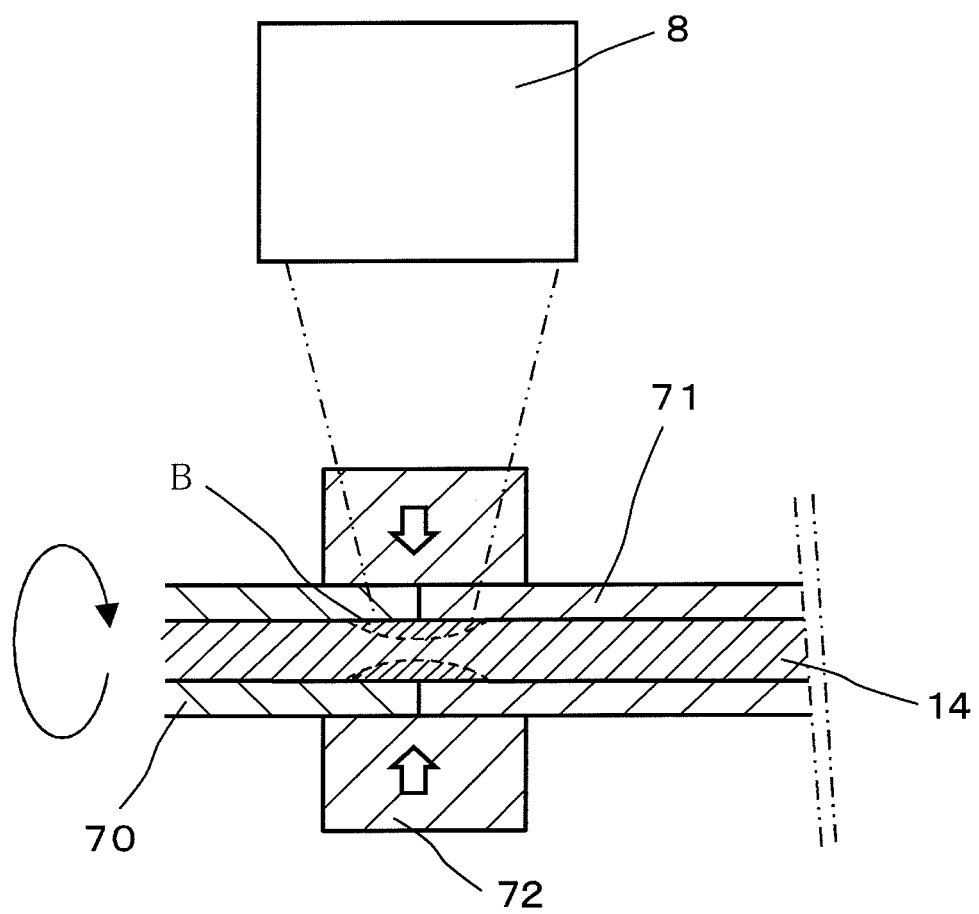
FIG. 21A is a sectional view of a welding section of a pair of catheters with an identical diameter before the welding.
Figure 21B:
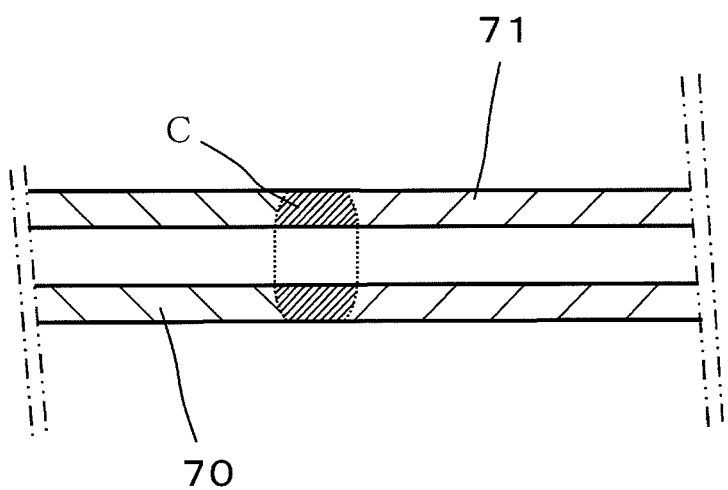
FIG. 21B is a sectional view of a welded section of the pair of catheters with the same diameter after the welding.

As illustrated in FIG. 21A, end faces of a pair of catheters with an identical diameter are butted against each other, and the catheters are applied with pressure from their radially outward side by a pressure tube 72 and are irradiated with laser light so as to be welded together without any level difference. The laser light penetrates through the pressure tube 72 and the pair of catheters, more specifically, the end portions of left- and right-hand tubes 70 and 71, and reaches the shaft 14 to heat same, so that the end portions of the left- and right-hand tubes 70 and 71 are fused and bonded together. FIG. 21B illustrates the thus-welded catheters with the same diameter.

In Embodiment 4, the force applied by the pressure tube 72 is made to be smaller than in the case of Embodiment 3. The function of the pressure tube used in Embodiment 4 is to allow the butted end portions of the pair of catheters to fuse and solidify while maintaining the outer diameter of the butted end portions. After the butted end portions of the pair of catheters are fused and solidified, the joint between the two catheters may have an outer diameter slightly smaller than the original diameter, but if the catheter joint has a smooth surface, the connected catheters can be satisfactorily inserted into the body via a blood vessel. If necessary, the force exerted by the pressure tube 72 may be set to be greater at the opposite end portions and smaller at the central portion by changing the material, thickness or configuration of the pressure tube 72, whereby the butted end portions of the pair of catheters can be made to fuse and solidify while maintaining the outer diameter of the butted end portions.

In FIGS. 21A and 21B, the shaft 14 generates heat to fuse the butted end portions of the pair of catheters. Alternatively, the pair of catheters may be made of a material having a predetermined laser absorption rate such that when irradiated with the laser light, not only the shaft 14 is heated but the catheters themselves are heated and fused to be connected together.

Figure 22A:
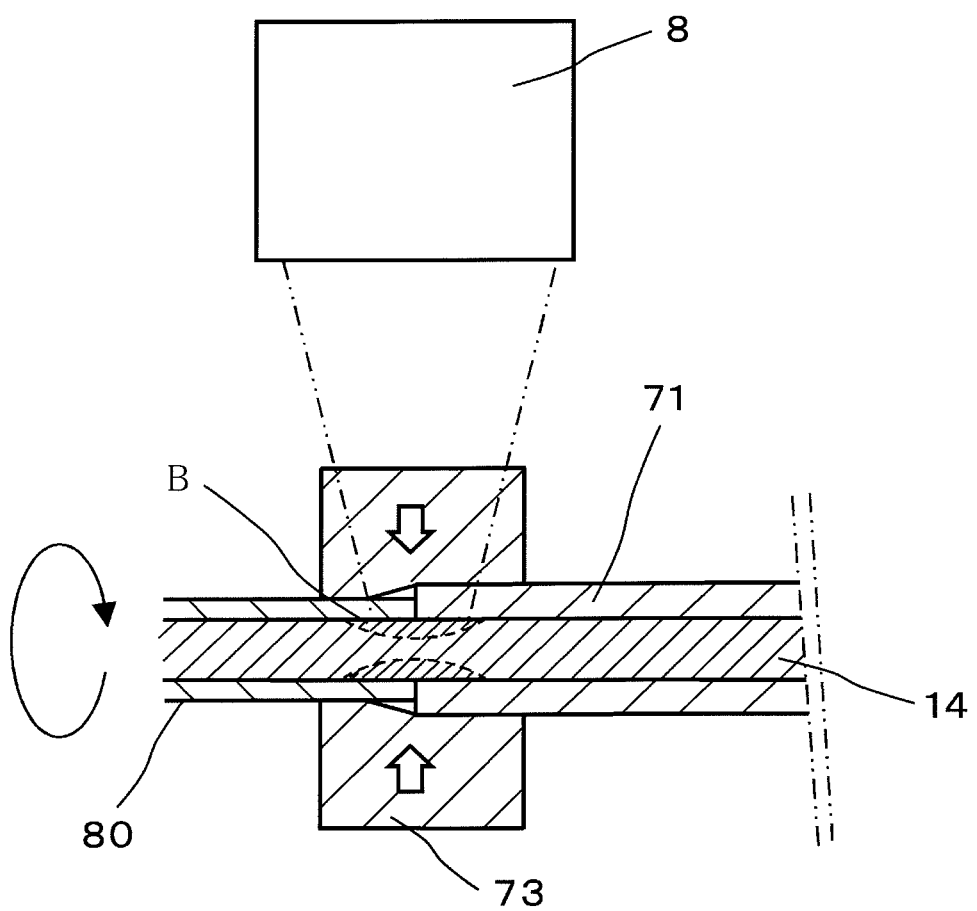
FIG. 22A is a sectional view of a welding section of a pair of catheters with different diameters before the welding.
Figure 22B:
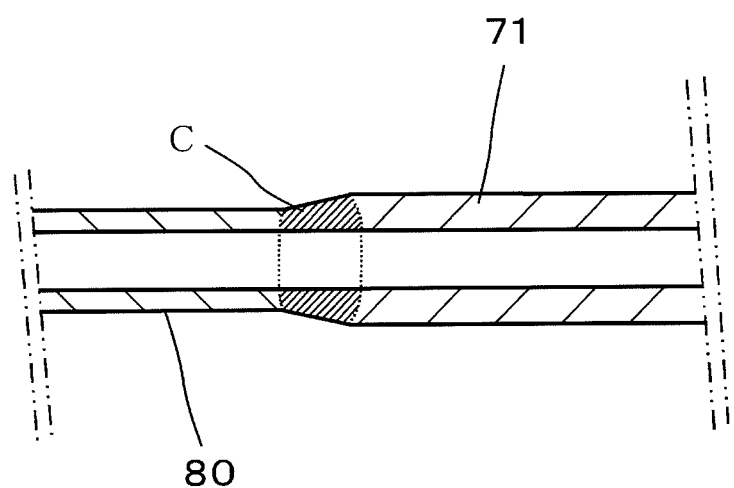
FIG. 22B is a sectional view of a welded section of the pair of catheters with different diameters after the welding.

As illustrated in FIG. 22A, end faces of a pair of catheters with different diameters may be butted against each other. The butted end portions of the catheters are applied with pressure from their radially outward side by a pressure tube 73 and then irradiated with the laser light so as to be welded together without a level difference at the joint. In FIG. 22A, the end face of the left-hand small-diameter tube 80 having an inner diameter equal to that of the right-hand tube 71 and an outer diameter smaller than that of the right-hand tube 71 is butted against the end face of the right-hand tube 80, and the pressure tube 73 is fitted around the butted end portions with a level difference to apply pressure to the butted end portions. Accordingly, the butted end portions of the tubes are fused into a shape indicated by C in FIG. 22B and are solidified in conical form.

Like Embodiment 2, this embodiment may also be provided with a camera for acquiring an image of the butted end portions of the pair of catheters, a monitor for displaying the image acquired by the camera, a storage, a registration-readout unit for registering and reading out the laser light radiation start and end positions in and from the storage, and a laser supporting unit configured to movably support the laser radiation unit, though not illustrated. While the image acquired by the camera is displayed on the monitor, the laser light radiation start and end positions are registered in the storage, and when the welding is to be executed, the laser light radiation start and end positions are read from the storage, and the butted end portions of the catheters are irradiated with the laser light from the laser light radiation start position to the laser light radiation end position by using the laser supporting unit. At this time, the catheters may be welded under welding conditions according to the diameters of the catheters such that the laser output with which the laser light is emitted to the large-diameter catheter is different from the laser output with which the laser light is emitted to the small-diameter catheter. This permits the butted ends of the two catheters with different diameters to be more smoothly connected to each other.

Figure 23A:
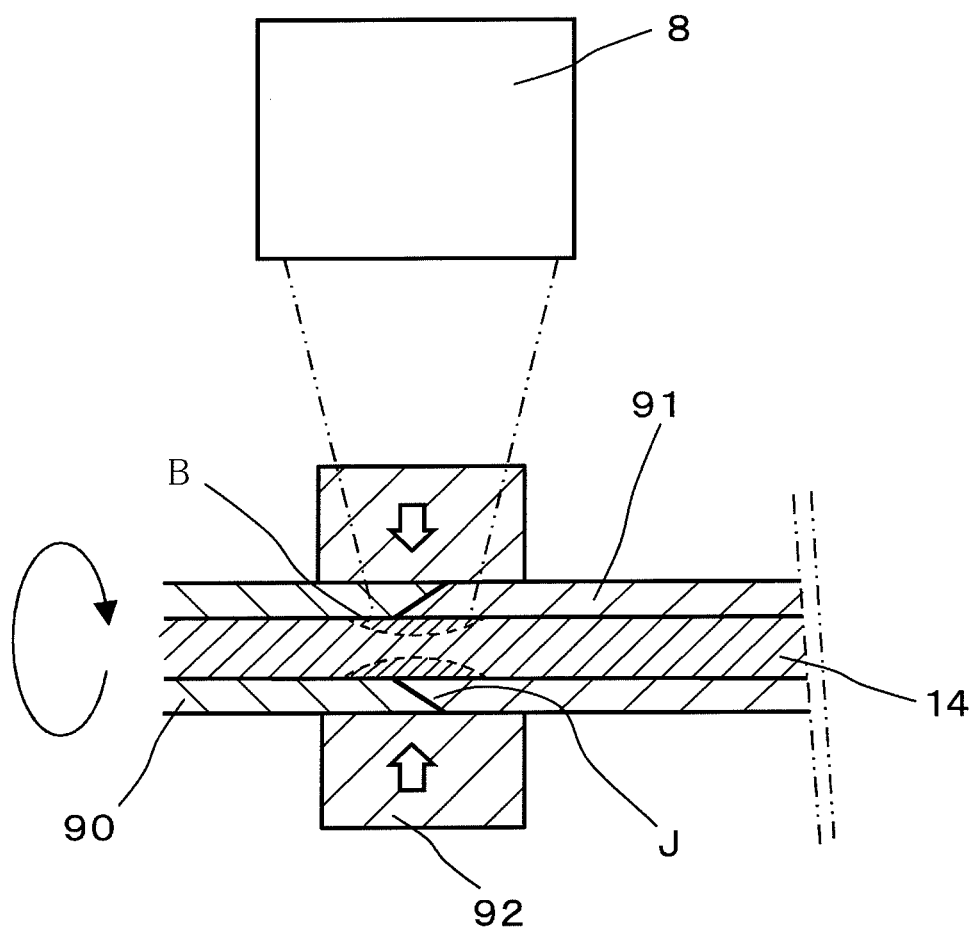
FIG. 23A is a sectional view of a welding section of a pair of catheters with an identical diameter before the welding.
Figure 23B:
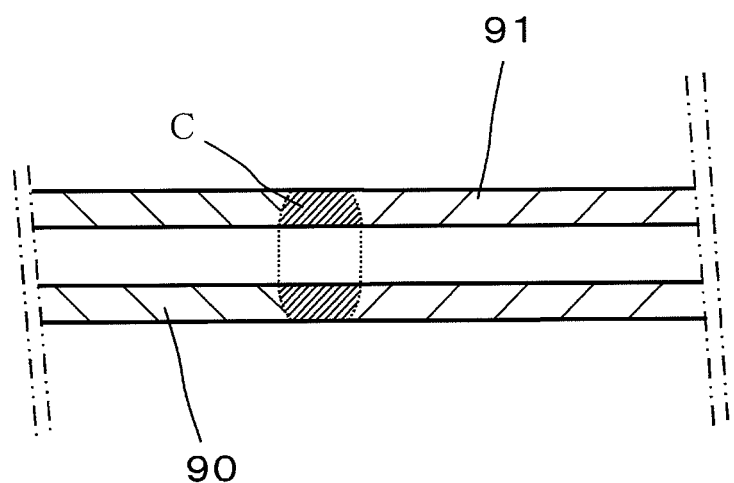
FIG. 23B is a sectional view of a welded section of the pair of catheters with the same diameter after the welding.
Figure 24A:
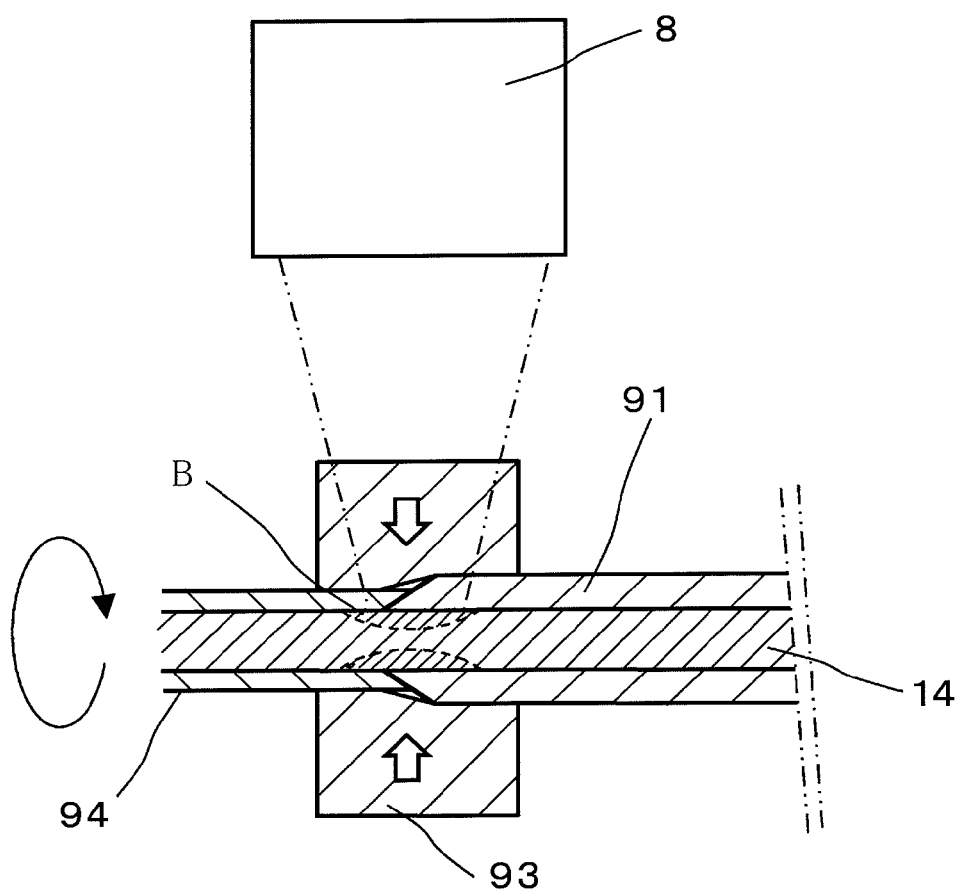
FIG. 24A is a sectional view of a welding section of a pair of catheters with different diameters before the welding.
Figure 24B:
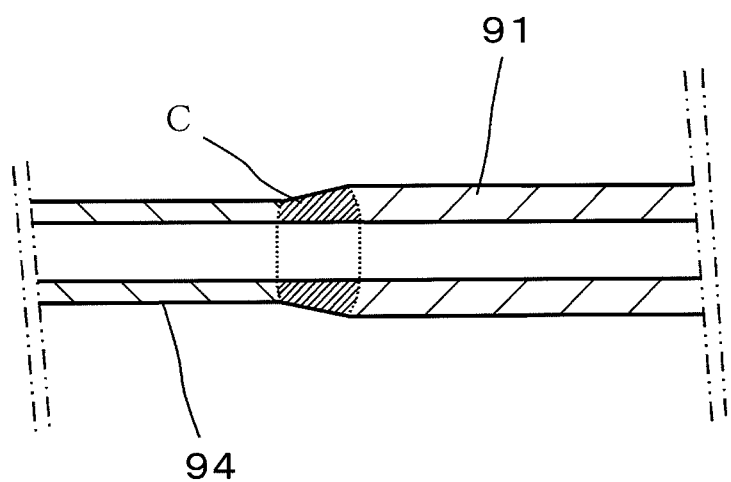
FIG. 24B is a sectional view of a welded section of the pair of catheters with different diameters after the welding.

Also, Embodiment 4 illustrated in FIGS. 21A, 21B, 22A and 22B may be modified as illustrated in FIGS. 23A, 23B, 24A and 24B. Specifically, the end faces of a pair of catheters may be formed as conical end faces J inclined with respect to the axis so that a convex conical end face of one tube may be received in a concave conical end face of the other tube. Where the concave conical end face of the other tube is made to fit over the convex conical end face of the one tube, the area of contact between the butted end faces increases, and since the two catheters are welded over the increased contact area, the two can be more firmly connected together. This applies not only to the case where the conical end faces of a pair of catheters with an identical diameter are butted against each other as illustrated in FIGS. 23A and 23B, but also to the case where the conical end faces of a pair of catheters with different outer diameters are butted against each other as illustrated in FIGS. 24A and 24B.

When welding the pair of catheters with different outer diameters, the laser radiation unit 8 may be moved in the axial direction of the catheters and the welding may be executed under conditions according to the diameters such that the laser output with which is the laser light is emitted to the large-diameter catheter differs from that with which the laser light is emitted to the small-diameter catheter, as stated above.

Figure 25:
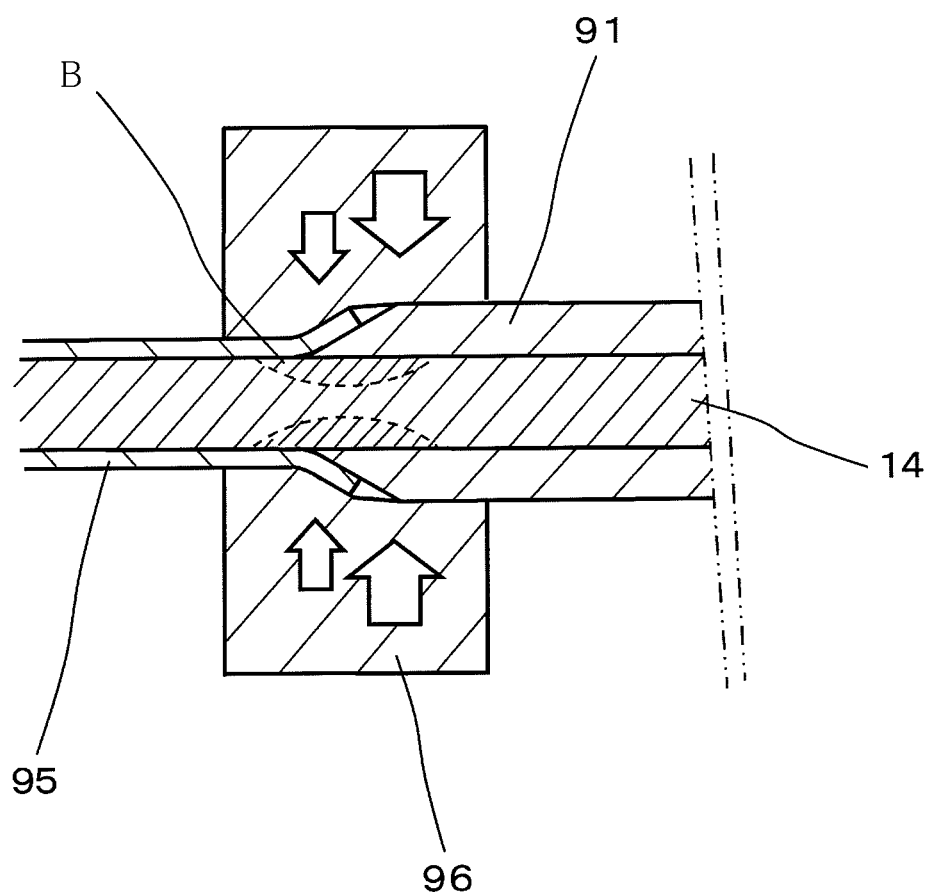
FIG. 25 is a sectional view of a welding section of a pair of catheters with different diameters before the welding.

Further, as illustrated in FIG. 25, the end face of one catheter 91 may be formed as a convex conical face while the end face of the other catheter 95 may be formed into a shape obtained by cutting the catheter 95 in a direction perpendicular to the axis. The end portion of the other catheter 95 is forced so as to be lapped over the conical face of the one catheter 91, and a pressure tube 96 is fitted around the catheters inclusive of the lap. Then, laser light is emitted from outside of the pressure tube 96 to the surface of the shaft 14, to heat the shaft 14 and thereby weld the lap. The configuration illustrated in FIG. 25 is advantageous in that special processing for forming the end face into a conical shape is required for the one catheter 91 only.

EXPLANATION OF REFERENCE SIGNS

1: balloon catheter manufacturing apparatus
2: cover
4: monitor
6: welding manipulator
8: laser radiation unit
10: laser supporting unit
10*a*: arm
12: camera
14, 48: shaft (heating shaft)
16: chuck (heating shaft rotation unit)
18: front shaft guide
20: center shaft guide
22: rear shaft guide
24: welding controller
26, 40, 50: balloon catheter
28, 42, 52: balloon
28*a*: body
28*b*, 28*c*, 42*a*, 42*b*, 52*a*, 52*b*: end portion
30*a*, 30*b*, 44, 46, 54: catheter tube
32*a*, 32*b*, 72, 73, 92, 93, 96: pressure tube
60: inner-side tube
61: outer-side tube
70, 80, 90, 94, 95: left-hand tube
71, 91: right-hand tube

The invention claimed is:
1. A balloon catheter manufacturing apparatus for welding a cylindrical balloon to a catheter tube inserted into the balloon, comprising:
   a heating shaft configured to receive the catheter tube, the heating shaft being capable of generating heat when irradiated with laser light sufficient to perform a weld;
   a heating shaft rotation unit rotatably supporting the heating shaft;
   a laser radiation unit configured to emit the laser light that penetrates through the balloon and the catheter tube to an outer peripheral surface of the heating shaft to heat the heating shaft sufficiently to perform the weld;
   a laser supporting unit configured to movably support the laser radiation unit;
   an annular pressure member made of an elastic material capable of transmitting the laser light therethrough, the pressure member having an inner diameter smaller than an outer diameter of an end portion of the balloon, the pressure member being fitted around the end portion of the balloon to apply pressure derived from elastic force to a welding section including the tip of the end portion of the balloon toward an axis of the pressure member;

a welding controller programmed to control the laser radiation unit to emit the laser light to penetrate through the pressure member, the balloon and the catheter to the outer peripheral surface of the heating shaft at a position corresponding to the welding section to heat the heating shaft sufficiently to properly perform the weld while causing the heating shaft rotation unit to rotate the heating shaft; and a storage capable of registering at least a laser light radiation start position, a laser output required for the tip of the balloon being welded to the catheter tube in a state that the tip of the balloon is buried in the catheter tube, and a laser light radiation end position therein;

wherein the welding controller reads out at least the laser light radiation start position, the laser output, and the laser light radiation end position from the storage when welding is to be executed, and causes the laser light to be radiated from the laser light radiation start position to the laser light radiation end position by using the laser supporting unit, to weld the welding section; and wherein the welding controller is programmed to control the laser radiation unit to vary output of the laser light emitted therefrom in accordance with a position to which the laser radiation unit is moved so that the output of the laser light at laser light radiation start position is high enough for the tip of the end portion of the balloon to be welded to the catheter tube as if the tip of the balloon is buried in the catheter tube, and lowers toward the laser light radiation end position, to weld the welding section;

whereby the tip of the end portion of the balloon buries into the catheter tube in a manner eliminating a level difference, so that the balloon and the catheter tube are welded together in the welding section such that the outer diameter of the tip of the end portion of the balloon is equal to the outer diameter of the catheter tube and the welding section has a smoothly-spreading-out profile.

2. The balloon catheter manufacturing apparatus according to claim 1, further comprising:

a camera configured to acquire an image of the welding section where the catheter tube is inserted into the end portion of the cylindrical balloon;

a monitor configured to display the image acquired by the camera; and a registration-readout unit configured to register and read out a laser light radiation start position and a laser light radiation end position in and from the storage;

wherein the welding controller is programmed to register the laser light radiation start and end positions in the storage by using the registration-readout unit while the image acquired by the camera is displayed on the monitor, and wherein the welding controller is programmed to read out the laser light radiation start and end positions from the storage by using the registration-readout unit when welding is to be executed, and cause the laser light to be radiated on the welding section where the end portion of the balloon is lapped over the catheter tube, from the laser light radiation start position to the laser light radiation end position by using the laser supporting unit, to weld the welding section.

3. The balloon catheter manufacturing apparatus according to claim 2, wherein the welding controller is programmed to register a predetermined position between the laser light radiation start and end positions and a welding condition applied to the predetermined position in the storage by using the registration-readout unit, and read out the registered welding condition from the storage to weld the welding section under the welding condition thus read out.

4. The balloon catheter manufacturing apparatus according to claim 3, wherein:

the welding controller is programmed to register an evaluation result obtained by actually executing welding under each welding condition registered in the storage, in a manner associated with the corresponding welding condition, and when the welding conditions are read out from the storage, the welding controller is programmed to control the monitor to display the welding conditions in descending order of the evaluation results so that a desired one of the welding conditions can be selected.

5. A catheter connection apparatus for welding a pair of catheter tubes lapped one over another, comprising:

a heating shaft configured to receive the pair of catheter tubes, the heating shaft being capable of generating heat when irradiated with laser light sufficient to perform a weld;

a heating shaft rotation unit rotatably supporting the heating shaft;

a laser radiation unit configured to emit the laser light that penetrates through the pair of catheter tubes to an outer peripheral surface of the heating shaft to heat the heating shaft sufficiently to perform the weld;

a laser supporting unit configured to movably support the laser radiation unit;

an annular pressure member made of an elastic material capable of transmitting the laser light therethrough, the pressure member having an inner diameter smaller than an outer diameter of an end portion of an outer-side one of the pair of catheter tubes, the pressure member being fitted around the end portion of the outer-side catheter tube to apply pressure derived from elastic force to a welding section including the tip of the end portion of the outer-side catheter tube toward an axis of the pressure member;

a welding controller programmed to control the laser radiation unit to emit the laser light to penetrate through the pressure member and the pair of catheter tubes to the outer peripheral surface of the heating shaft at a position corresponding to the welding section to heat the heating shaft sufficiently to properly perform the weld while causing the heating shaft rotation unit to rotate the heating shaft; and a storage capable of registering at least a laser light radiation start position, a laser output required for the tip of the end portion of the outer-side one of the pair of catheter tube being welded to the inner-side one of the pair of catheter tube in a state that the tip of the end portion of the outer-side one is buried in the inner-side one of the pair of catheter tube, and a laser light radiation end position therein;

wherein the welding controller reads out at least the laser light radiation start position, the laser output, and the laser light radiation end position from the storage when welding is to be executed, and causes the laser light to be radiated on the welding section where the end portion of the pair of the catheter tubes lapped one over another, from the laser light radiation start position to the laser light radiation end position by using the laser supporting unit, to weld the welding section; and wherein the welding controller is programmed to control the laser radiation unit to vary output of the laser light emitted therefrom in accordance with a position to which the laser radiation unit is moved so that the output of the laser light at laser light radiation start position is high enough for the tip of the end portion of the outer-side one of the pair of catheter tube to be welded to the inner-side one of the pair of catheter tube as if the tip of the end portion of the outer-side one is buried in the inner-side one of the pair of catheter tube, and lowers toward the laser light radiation end position, to weld the welding section;

whereby the tip of the outer-side catheter buries into the inner-side catheter tube in a manner eliminating a level difference, so that the outer-side and the inner-side catheter tubes are welded together in the welding section such that the outer diameter of the tip of the outer-side catheter is equal to the outer diameter of the inner-side catheter tube and the welding section has an spreading-out profile.

6. The catheter connection apparatus according to claim 5, further comprising:
- a camera configured to acquire an image of the welding section corresponding to the end portions of the pair of catheter tubes;
- a monitor configured to display the image acquired by the camera; and
- a registration-readout unit configured to register and read out a laser light radiation start position and a laser light radiation end position in and from the storage, wherein:
the welding controller is programmed to register the laser light radiation start and end positions in the storage by using the registration-readout unit while the image acquired by the camera is displayed on the monitor,
wherein the welding controller is programmed to read out the laser light radiation start and end positions from the storage by using the registration-readout unit when welding is to be executed, and cause the laser light to be radiated on the welding section corresponding to the end portions of the pair of catheters, from the laser light radiation start position to the laser light radiation end position by using the laser supporting unit, to weld the welding section.

7. The catheter connection apparatus according to claim 5, wherein the welding controller is programmed to register a predetermined position between the laser light radiation start and end positions and a welding condition applied to the predetermined position in the storage by using the registration-readout unit, and read out the registered welding condition from the storage to weld the welding section under the welding condition thus read out.

8. The catheter connection apparatus according to claim 7, wherein:
the welding controller is programmed to register an evaluation result obtained by actually executing welding under each welding condition registered in the storage, in a manner associated with the corresponding welding condition, and
when the welding conditions are read out from the storage, the welding controller is programmed to control the monitor to display the welding conditions in descending order of the evaluation results so that a desired one of the welding conditions can be selected.

* * * * *